(12) United States Patent
Sykes et al.

(10) Patent No.: US 11,160,958 B2
(45) Date of Patent: *Nov. 2, 2021

(54) MEDICAL INFLATION SYSTEMS AND METHODS

(71) Applicant: Merit Medical Systems, Inc., South Jordan, UT (US)

(72) Inventors: Kenneth Sykes, Bluffdale, UT (US); Gregory R. McArthur, Sandy, UT (US); Richard P. Jenkins, Bluffdale, UT (US); David Butts, Riverton, UT (US); Steven Weir, Sandy, UT (US); Jon Davis, Sandy, UT (US); John William Hall, North Salt Lake, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 147 days.

This patent is subject to a terminal disclaimer.

(21) Appl. No.: 15/903,372

(22) Filed: Feb. 23, 2018

(65) Prior Publication Data

US 2018/0243540 A1    Aug. 30, 2018

Related U.S. Application Data

(60) Provisional application No. 62/463,285, filed on Feb. 24, 2017, provisional application No. 62/564,089, filed on Sep. 27, 2017.

(51) Int. Cl.
  *A61M 25/10*    (2013.01)

(52) U.S. Cl.
  CPC ............... *A61M 25/10182* (2013.11); *A61M 25/10184* (2013.11); *A61M 2205/3334* (2013.01)

(58) Field of Classification Search
  CPC ............ A61M 5/3232; A61M 5/3234; A61M 5/3137; A61M 2005/3242;
  (Continued)

(56) References Cited

U.S. PATENT DOCUMENTS 4,161,891 A    7/1979  Bossert
4,651,738 A *  3/1987  Demer .............. A61M 25/1018
                                               604/920
(Continued)

FOREIGN PATENT DOCUMENTS

EP    0213765    3/1987
EP    0396353    3/1995
(Continued)

OTHER PUBLICATIONS

Office Action dated Aug. 21, 2019 for U.S. Appl. No. 15/669,033.
(Continued)

*Primary Examiner* — Lauren P Farrar
*Assistant Examiner* — Hamza A Darb
(74) *Attorney, Agent, or Firm* — Stoel Rives LLP

(57)    ABSTRACT

Devices used to pressurize, depressurize, or otherwise displace fluid are disclosed. The devices may be configured to displace fluid in order to inflate or deflate a medical device, such as a balloon. The devices further include a crank member for providing a mechanical advantage when pressurizing or otherwise displacing fluid.

21 Claims, 30 Drawing Sheets

(58) Field of Classification Search
CPC .. A61M 2005/3239; A61M 2005/3231; A61M 5/322; A61M 25/10182; A61M 25/10184; A61M 2205/3334; A61M 5/315; A61M 5/31576; A61M 5/31511; A61M 5/31583
See application file for complete search history.

(56) References Cited

U.S. PATENT DOCUMENTS

| | | | |
|---|---|---|---|
| 4,655,749 | A | 4/1987 | Fischione |
| 4,723,938 | A | 2/1988 | Goodin et al. |
| 4,758,223 | A | 7/1988 | Rydell |
| 4,781,192 | A | 11/1988 | Demer |
| 4,919,121 | A | 4/1990 | Rydell et al. |
| 4,940,459 | A | 7/1990 | Noce |
| 5,047,015 | A | 9/1991 | Foote et al. |
| 5,057,078 | A | 10/1991 | Foote et al. |
| 5,150,853 | A | 9/1992 | Bernard et al. |
| 5,163,904 | A | 11/1992 | Lampropoulos et al. |
| 5,209,732 | A | 5/1993 | Lampropoulos et al. |
| 5,213,115 | A | 5/1993 | Zytkovicz et al. |
| 5,306,248 | A | 4/1994 | Barrington |
| 5,472,424 | A | 12/1995 | Lampropoulos et al. |
| 5,685,848 | A | 11/1997 | Robinson et al. |
| 5,741,229 | A | 4/1998 | Robinson et al. |
| 5,904,342 | A | 5/1999 | Laarman |
| 6,106,496 | A | 8/2000 | Arnissolle |
| 6,471,671 | B1 | 10/2002 | Urick et al. |
| 6,834,670 | B2 | 12/2004 | Rosine et al. |
| 7,041,084 | B2 | 5/2006 | Fojtik |
| 8,372,030 | B2 | 2/2013 | Dixon et al. |
| 8,545,442 | B2 | 10/2013 | Lampropoulos et al. |
| 8,758,294 | B2 | 7/2014 | Kim et al. |
| 2004/0084084 | A1 | 5/2004 | Rosine et al. |
| 2005/0234493 | A1 | 10/2005 | Carr et al. |
| 2008/0077075 | A1* | 3/2008 | Moreira .......... A61M 25/10184 604/19 |
| 2009/0151484 | A1 | 6/2009 | Mullen et al. |
| 2010/0211007 | A1 | 8/2010 | Lesch, Jr. et al. |
| 2010/0298836 | A1 | 11/2010 | Jordan |
| 2013/0123693 | A1 | 5/2013 | Lampropoulos et al. |
| 2013/0165899 | A1 | 6/2013 | Haueter et al. |
| 2013/0331780 | A1 | 12/2013 | Lampropoulos et al. |
| 2014/0074141 | A1 | 3/2014 | Johnson et al. |
| 2014/0081205 | A1 | 3/2014 | Kanner et al. |
| 2014/0088499 | A1 | 3/2014 | Lampropoulos et al. |
| 2014/0168958 | A1* | 6/2014 | Unger .................... F21L 13/06 362/183 |
| 2015/0051543 | A1 | 2/2015 | Chadwick et al. |
| 2016/0199091 | A1 | 7/2016 | Pigott |
| 2018/0036520 | A1* | 2/2018 | Teitelbaum ..... A61M 25/10182 |
| 2018/0264509 | A1 | 9/2018 | Pauser et al. |
| 2019/0240418 | A1 | 8/2019 | Takahashi et al. |
| 2020/0230379 | A1 | 7/2020 | Simmons et al. |
| 2020/0282191 | A1 | 9/2020 | McArthur et al. |

FOREIGN PATENT DOCUMENTS

| | | |
|---|---|---|
| JP | 61009561 | 12/1986 |
| WO | 2009128393 | 10/2009 |
| WO | 2012094403 | 7/2012 |
| WO | 2015023923 | 2/2015 |
| WO | 2015134568 | 9/2015 |

OTHER PUBLICATIONS

International Search Report and Written Opinion dated Nov. 15, 2017 for PCT/US2017/045456.
International Search Report and Written Opinion dated Jun. 27, 2018 for PCT/US2018/019378.
International Search Report and Written Opinion dated May 20, 2020 for PCT/US2020/013921.
European Search Report dated Mar. 5, 2020 for EP17837742.0.
Office Action dated Feb. 13, 2020 for U.S. Appl. No. 15/669,033.
European Search Report dated Nov. 23, 2020 for EP18756701.1.
International Search Report and Written Opinion dated Jun. 30, 2020 for PCT/US2020/020996.
Office Action dated Feb. 25, 2021 for U.S. Appl. No. 15/669,033.
Office Action dated Nov. 6, 2020 for U.S. Appl. No. 15/669,033.

* cited by examiner

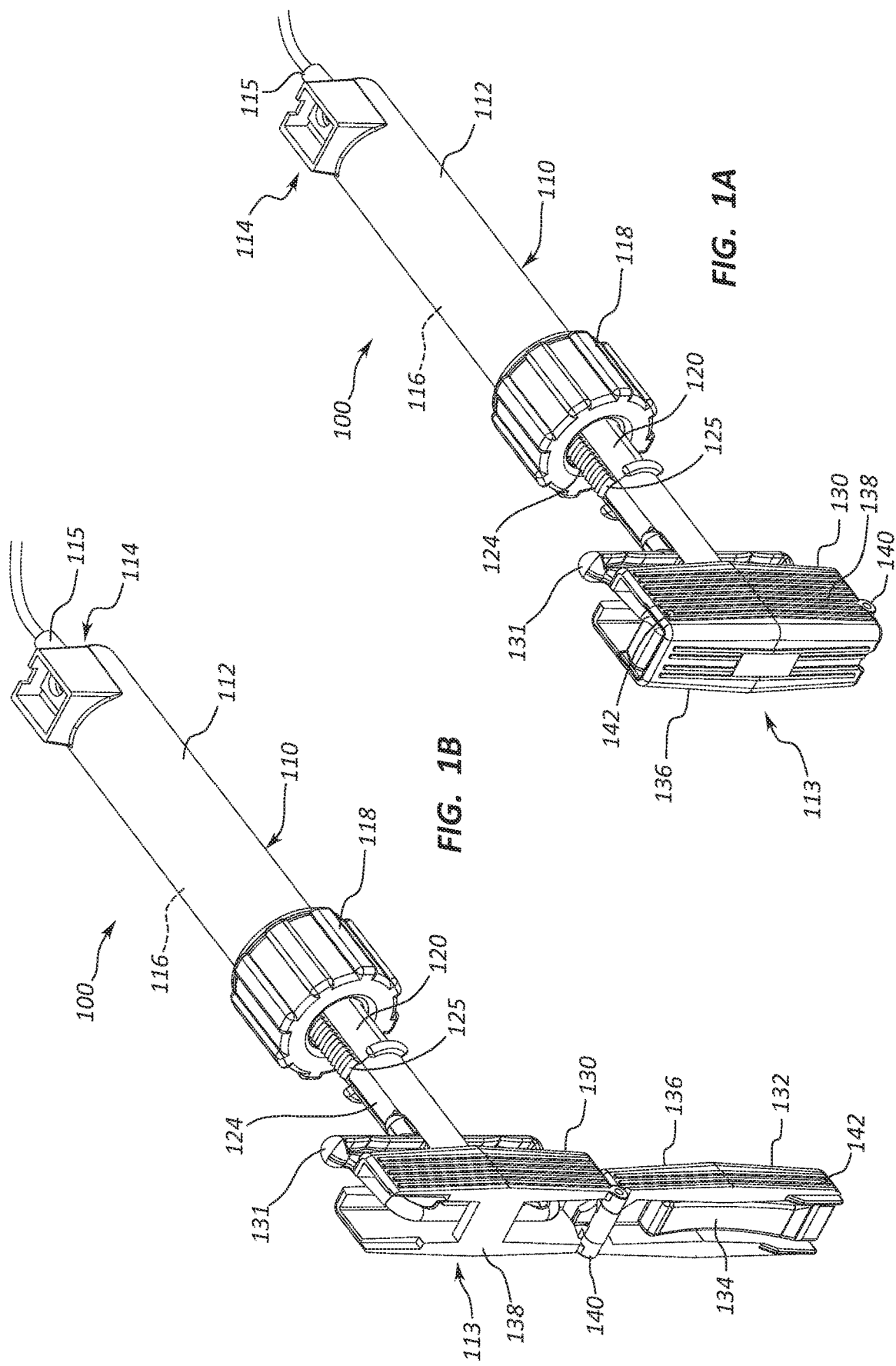

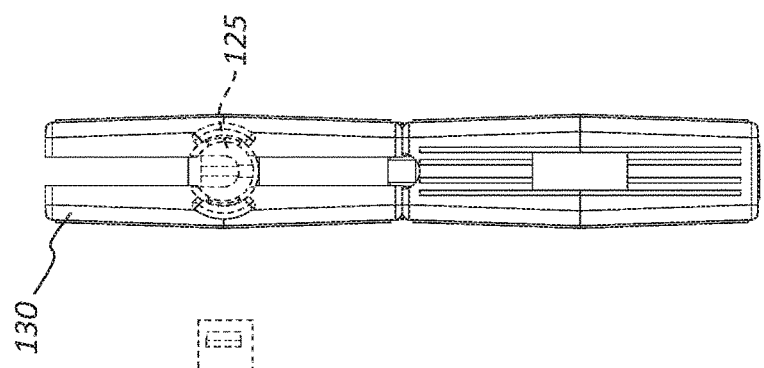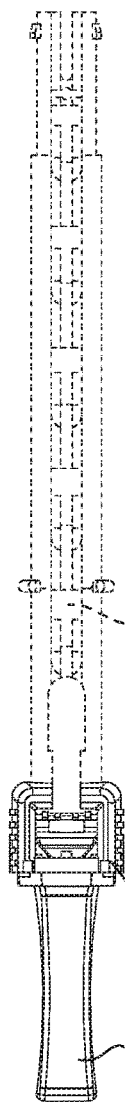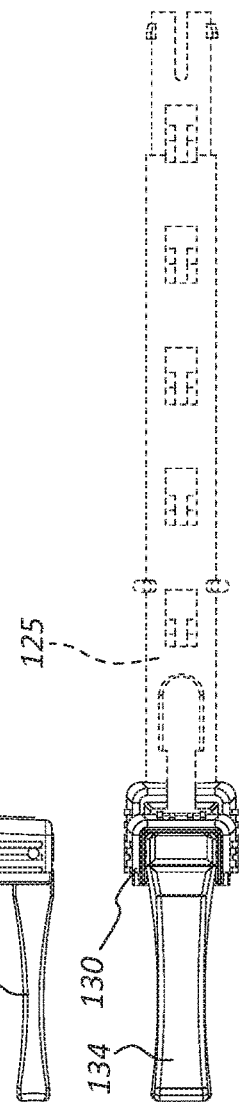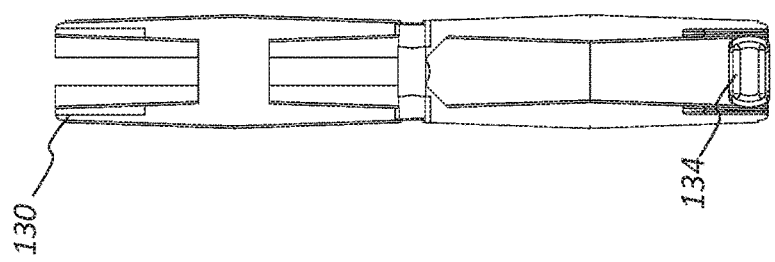

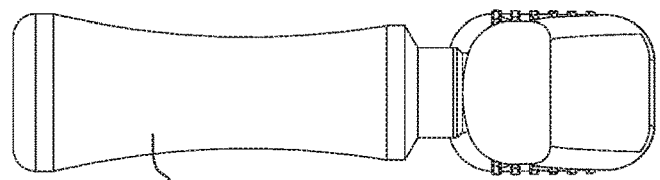
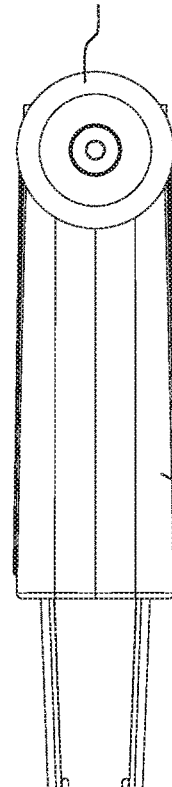
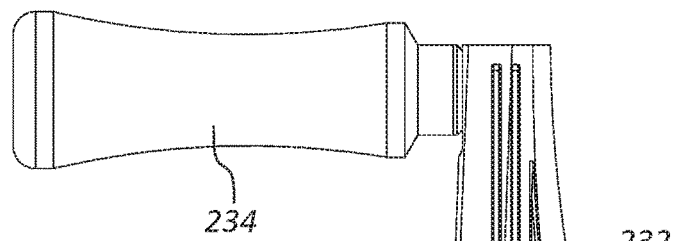
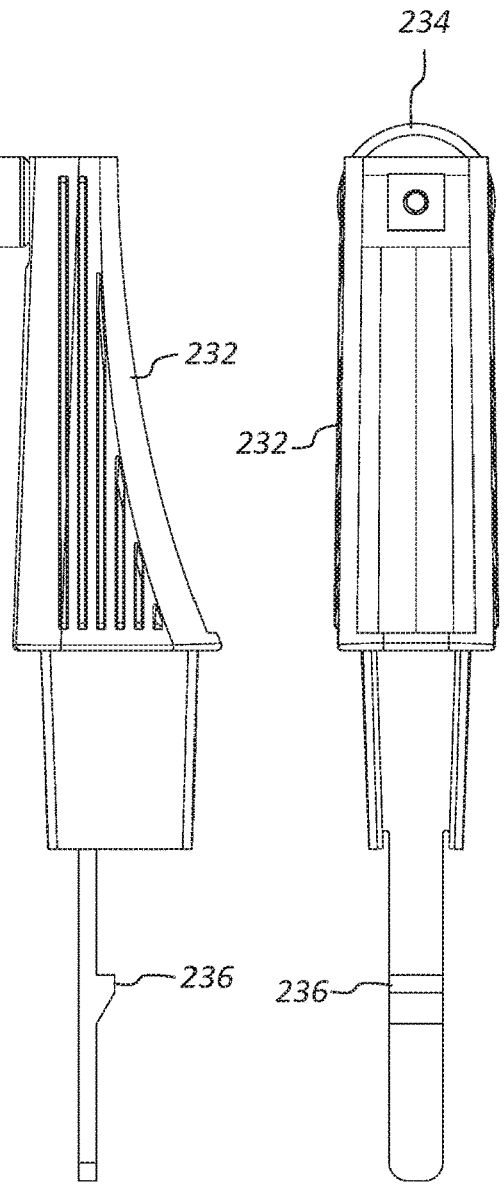
FIG. 2I
FIG. 2G  FIG. 2F  FIG. 2H
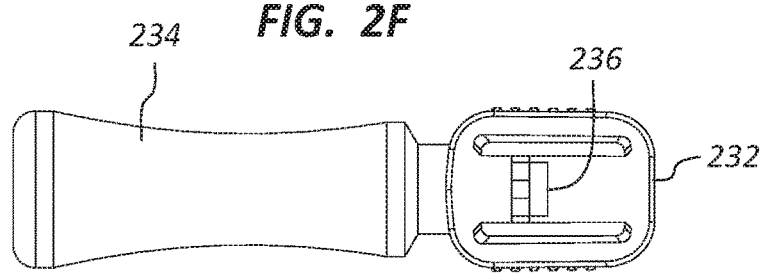
FIG. 2J

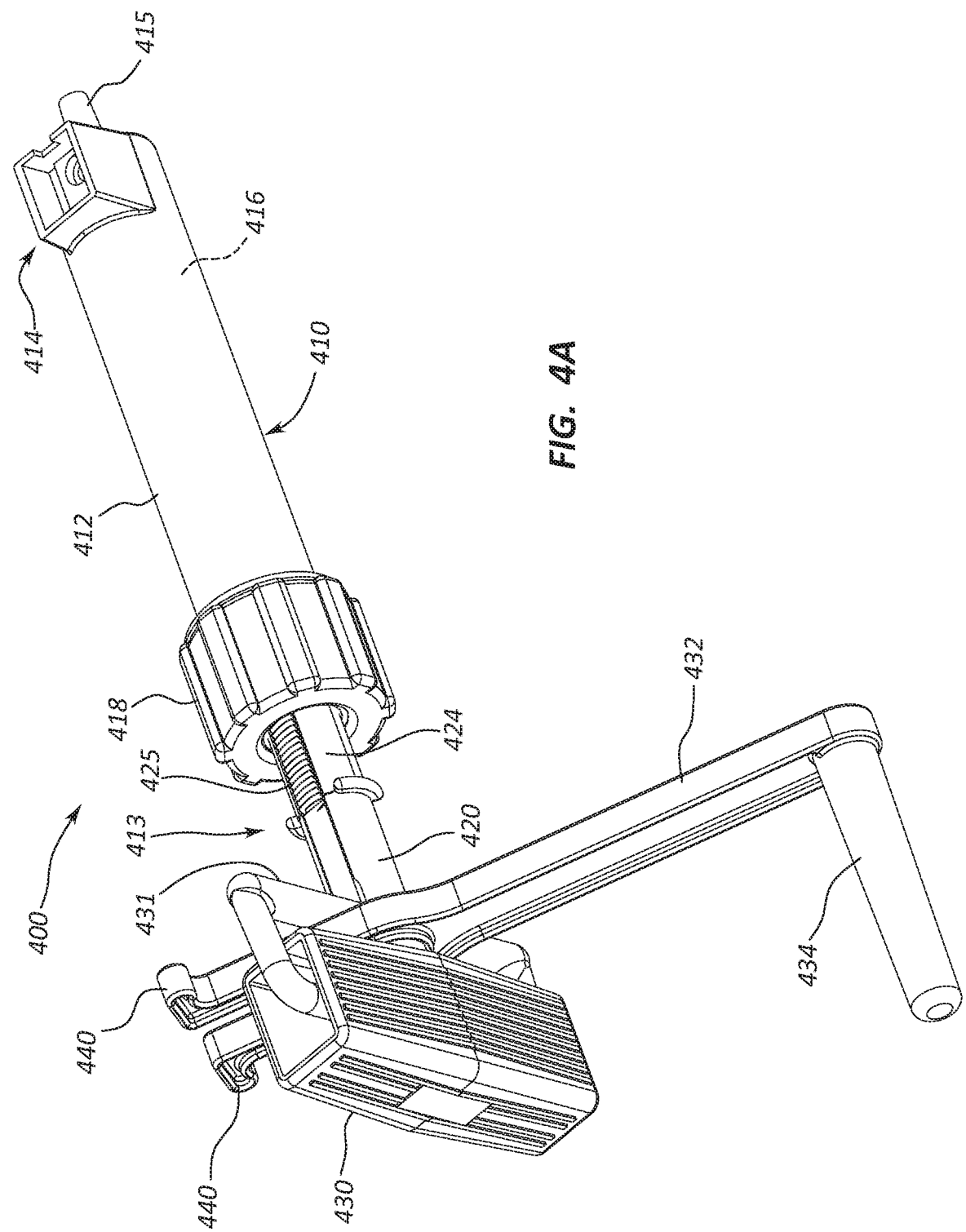

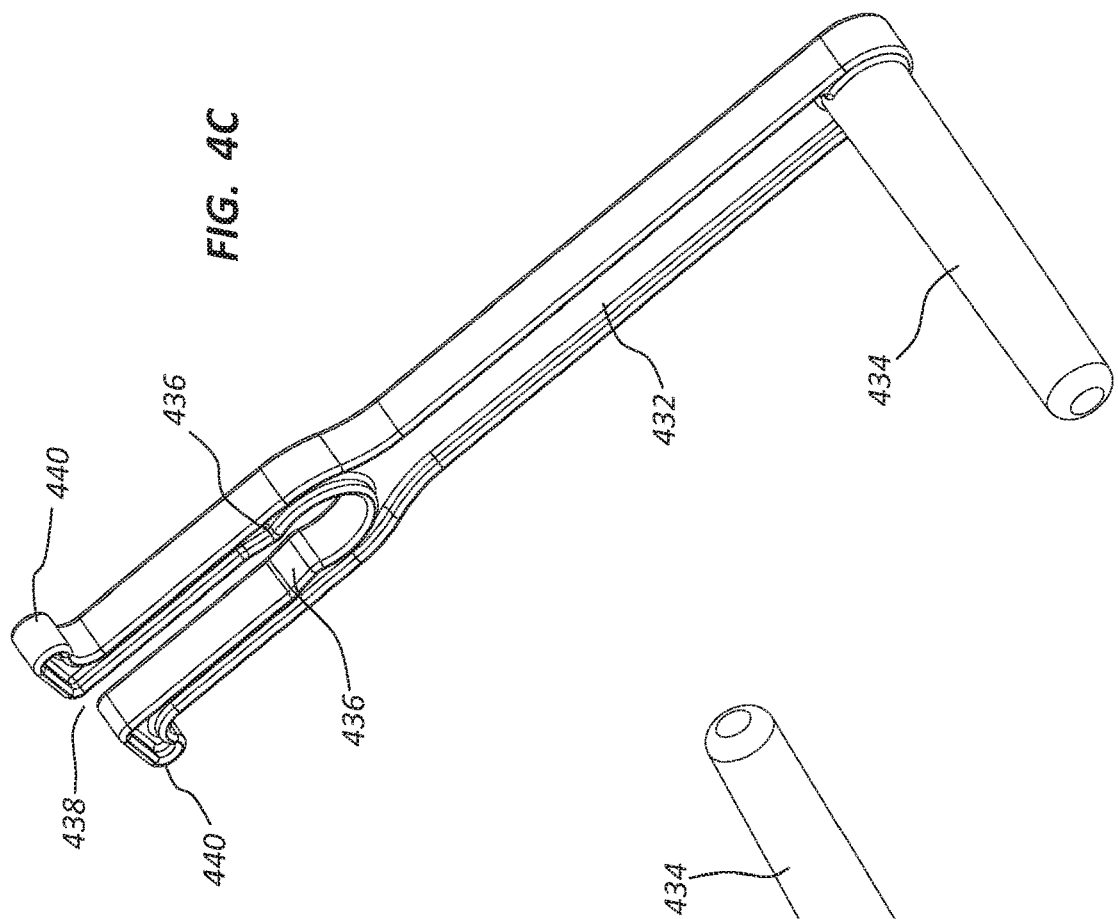
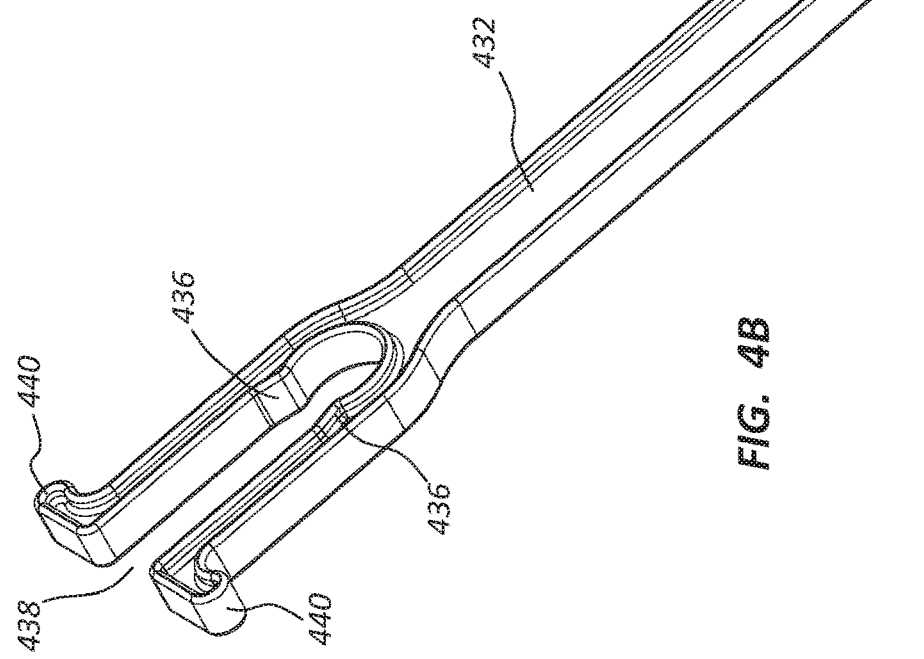

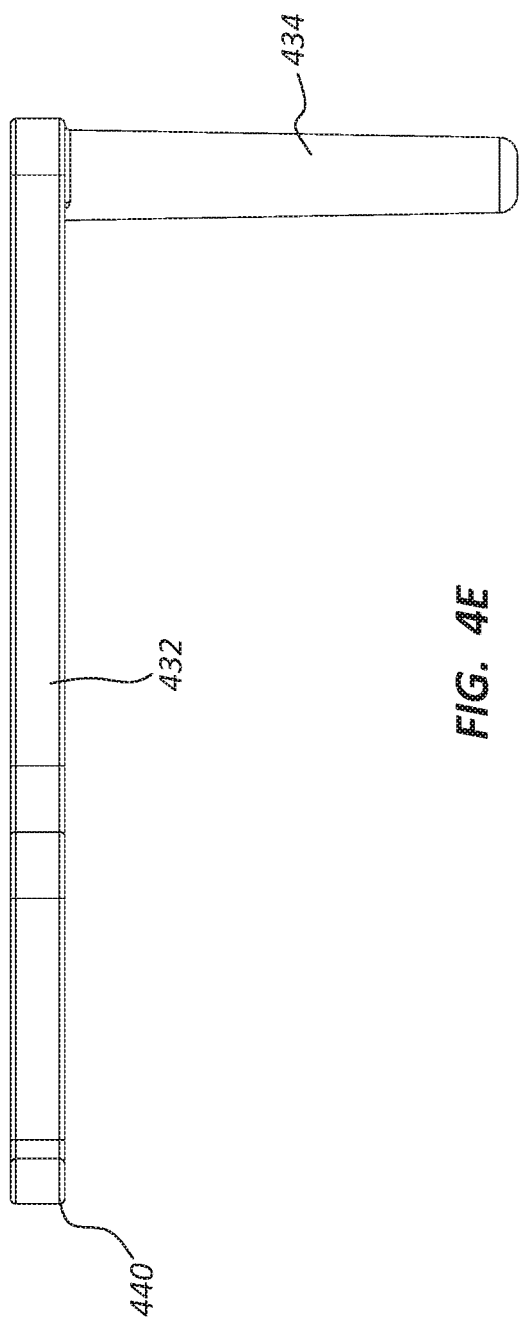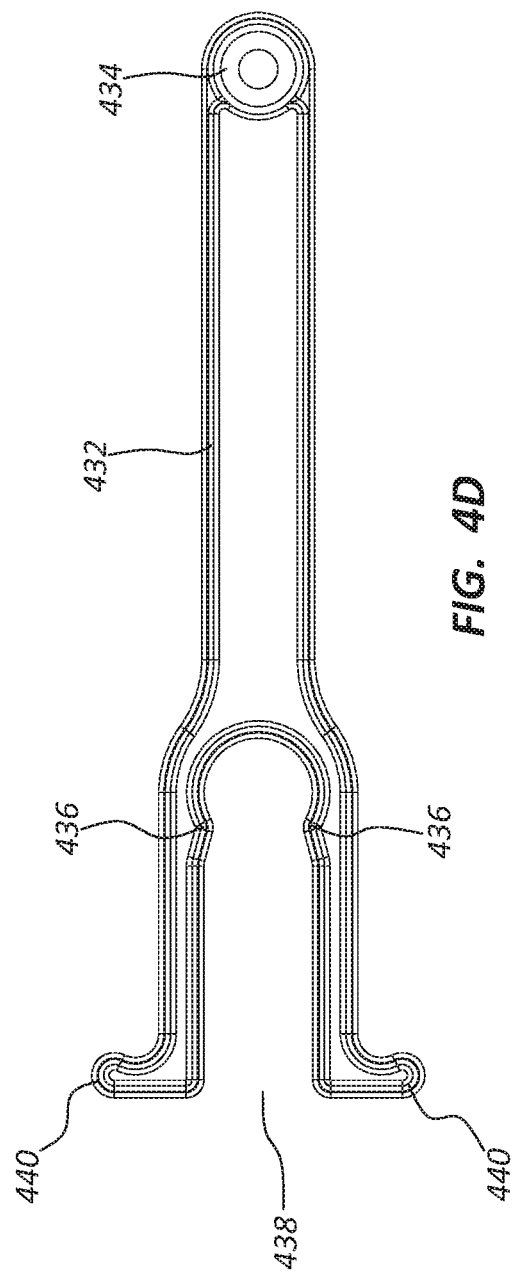

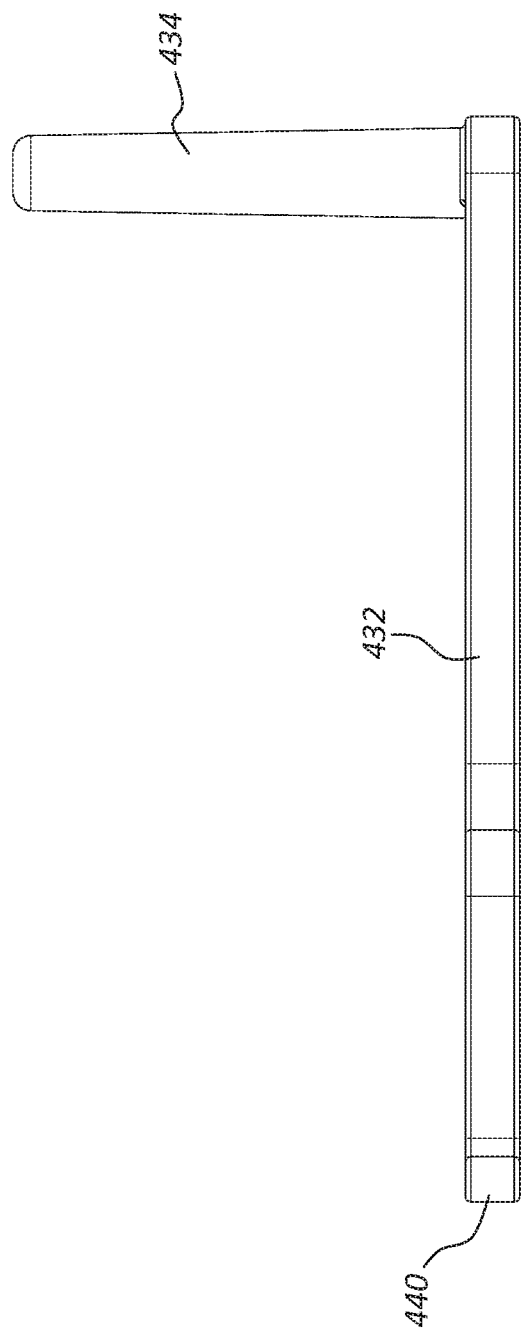
FIG. 4F
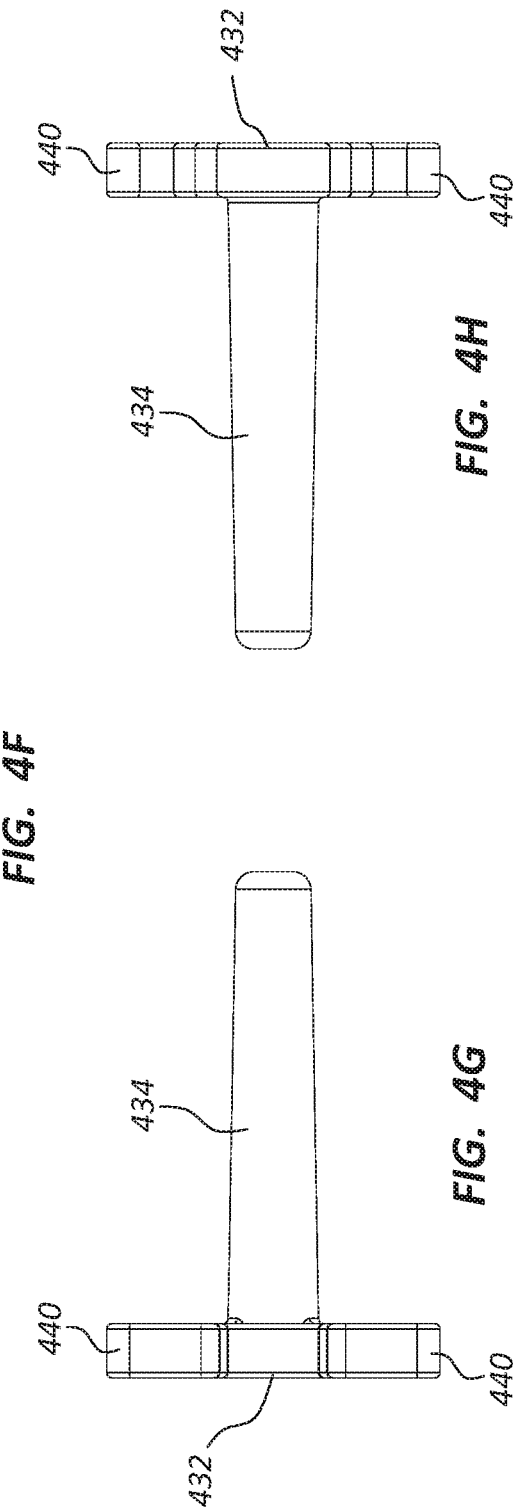
FIG. 4H
FIG. 4G

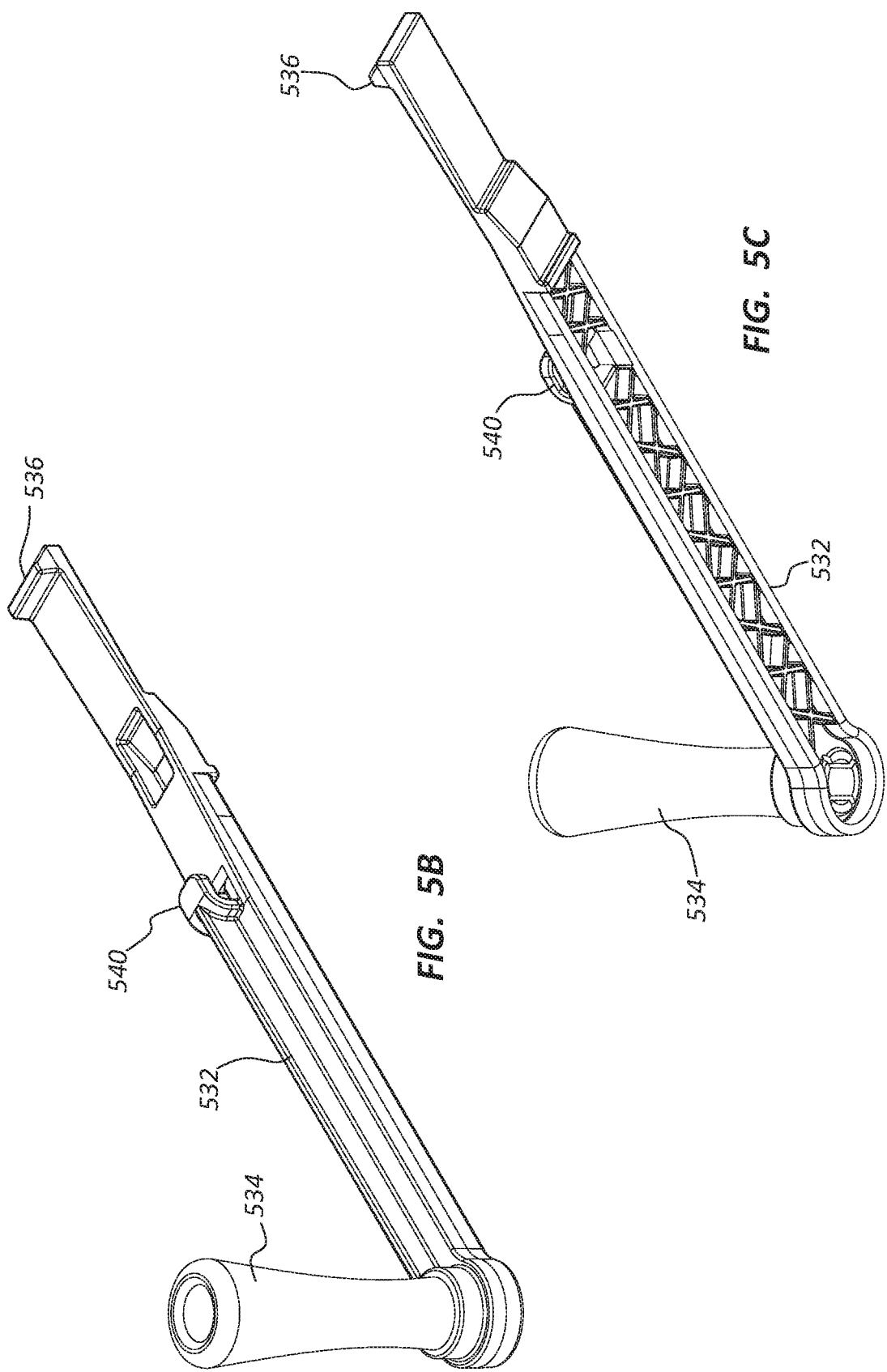

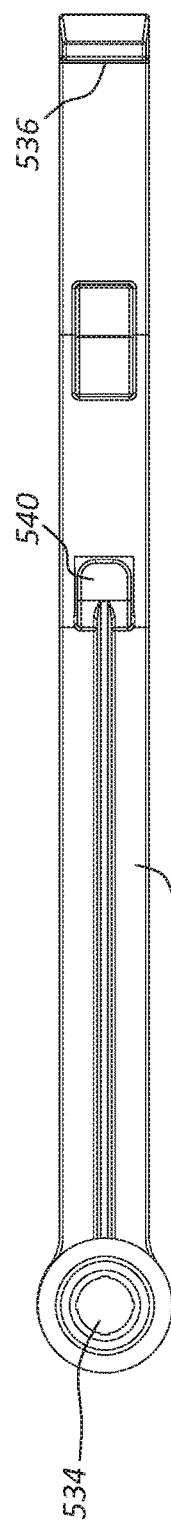
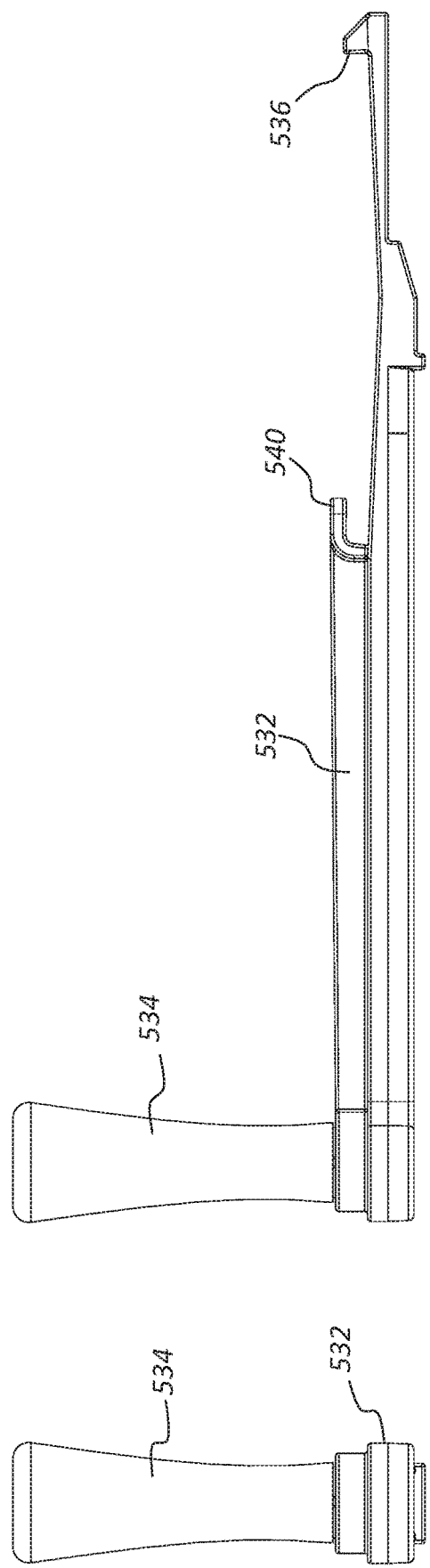
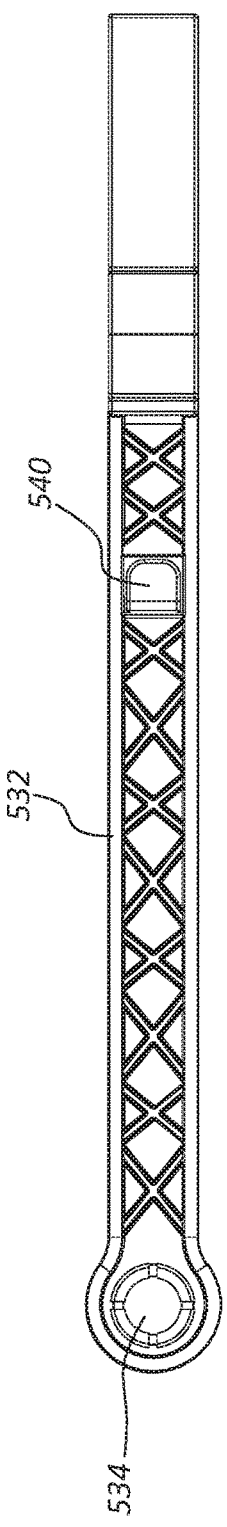
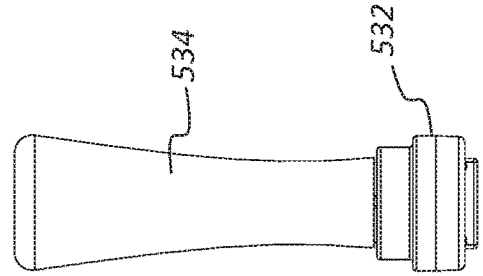
FIG. 5E
FIG. 5D
FIG. 5F
FIG. 5G

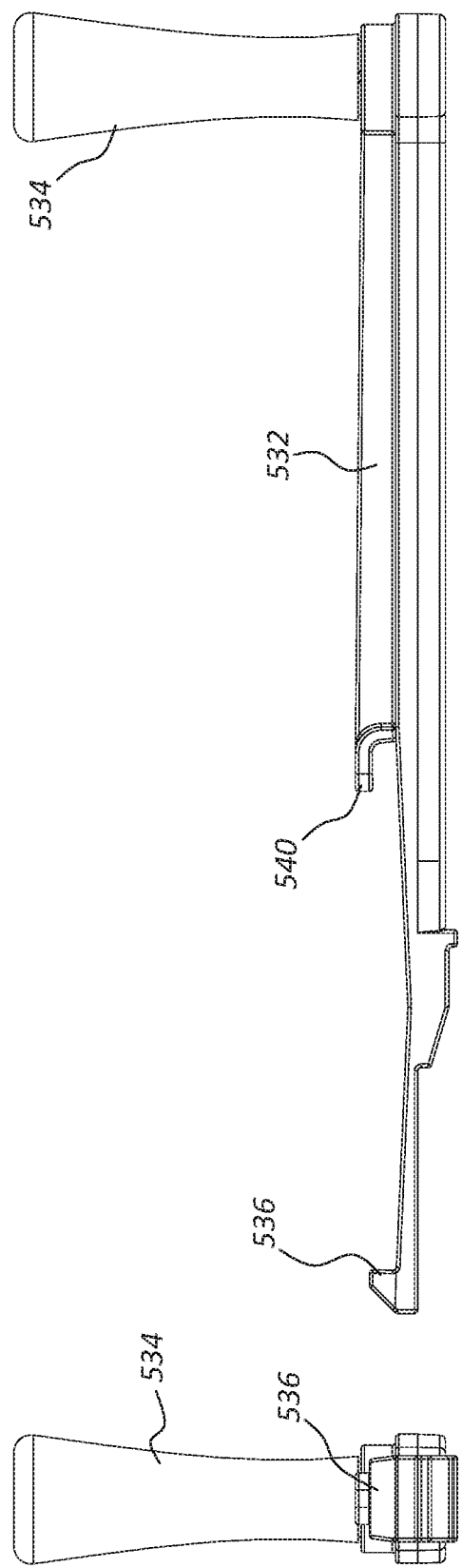

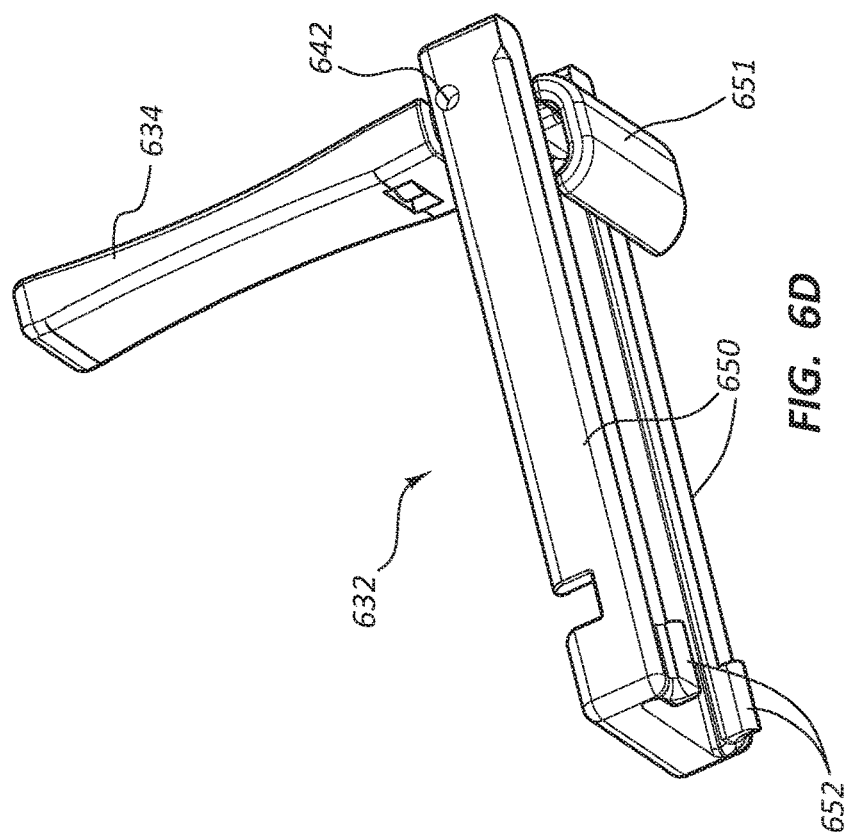
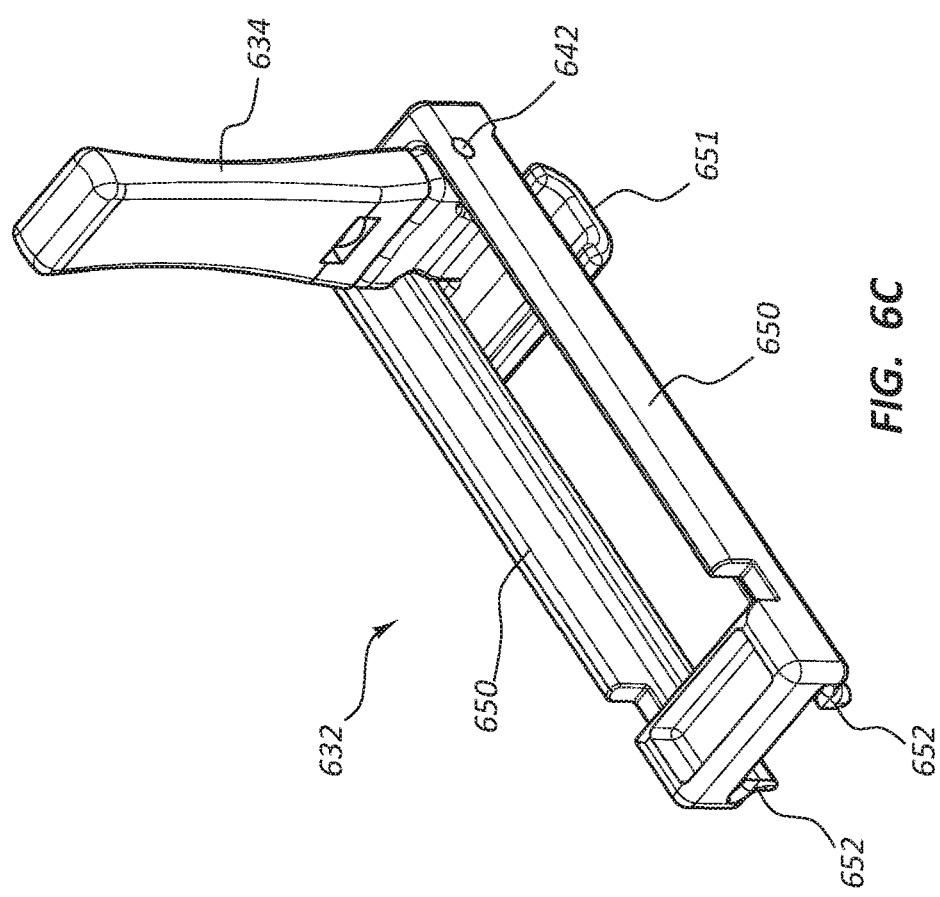
FIG. 6C
FIG. 6D

MEDICAL INFLATION SYSTEMS AND METHODS

RELATED APPLICATIONS

This application claims priority to U.S. Provisional Application No. 62/463,285, filed on Feb. 24, 2017 and titled "Medical Inflation Systems and Methods" and U.S. Provisional Application No. 62/564,089, filed on Sep. 27, 2017 and titled "Medical Inflation Systems and Methods," both of which are hereby incorporated by reference in their entireties.

TECHNICAL FIELD

The present disclosure relates generally to devices used to pressurize, depressurize, or otherwise displace fluid, particularly in medical devices. More specifically, the present disclosure relates to high-pressure devices used to pressurize, depressurize, or otherwise displace fluid along a line in order to inflate or deflate a medical device, such as a balloon.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 1A is a perspective view of an inflation device.

FIG. 1B is a perspective view of the inflation device of FIG. 1A, shown in a partially deployed state.

FIG. 1I is a side elevation view of the handle of the inflation device of FIG. 1A, shown in a deployed state.

FIG. 1J is a right side view of the handle of the inflation device of FIG. 1A, shown in a deployed state.

FIG. 1K is a left side view of the handle of the inflation device of FIG. 1A, shown in a deployed state.

FIG. 1L is a top view of the handle of the inflation device of FIG. 1A, shown in a deployed state.

FIG. 1M is a bottom view of the handle of the inflation device of FIG. 1A, shown in a deployed state.

FIG. 2F is a side view of the crank member of the inflation device assembly of FIG. 2A.

FIG. 2G is a top view of the crank member of the inflation device assembly of FIG. 2A.

FIG. 2H is a bottom view of the crank member of the inflation device assembly of FIG. 2A.

FIG. 2I is a back end view of the crank member of the inflation device assembly of FIG. 2A.

FIG. 2J is a front end view of the crank member of the inflation device assembly of FIG. 2A.

FIG. 4A is a perspective view of another inflation device assembly.

FIG. 4B is a first perspective view of the crank member of the inflation device assembly of FIG. 4A.

FIG. 4C is a second perspective view of the crank member of the inflation device assembly of FIG. 4A.

FIG. 4D is a top plan view of the crank member of the inflation device assembly of FIG. 4A.

FIG. 4E is a left side view of the crank member of the inflation device assembly of FIG. 4A.

FIG. 4F is a right side view of the crank member of the inflation device assembly of FIG. 4A.

FIG. 4G is a front end view of the crank member of the inflation device assembly of FIG. 4A.

FIG. 4H is a rear view of the crank member of the inflation device assembly of FIG. 4A.

FIG. 5B is a first perspective view of the crank member of the inflation device assembly of FIG. 5A.

FIG. 5C is a second perspective view of the crank member of the inflation device assembly of FIG. 5A.

FIG. 5D is a left side elevation view of the crank member of the inflation device assembly of FIG. 5A.

FIG. 5E is a top plan view of the crank member of the inflation device assembly of FIG. 5A.

FIG. 5F is a bottom view of the crank member of the inflation device assembly of FIG. 5A.

FIG. 5G is a rear end view of the crank member of the inflation device assembly of FIG. 5A.

FIG. 5H is a right side elevation view of the crank member of the inflation device assembly of FIG. 5A.

FIG. 5I is a front end view of the crank member of the inflation device assembly of FIG. 5A.

FIG. 6C is a first perspective view of the crank member of FIG. 6A.

FIG. 6D is a second perspective view of the crank member of FIG. 6A.

DETAILED DESCRIPTION

Figure 1C:
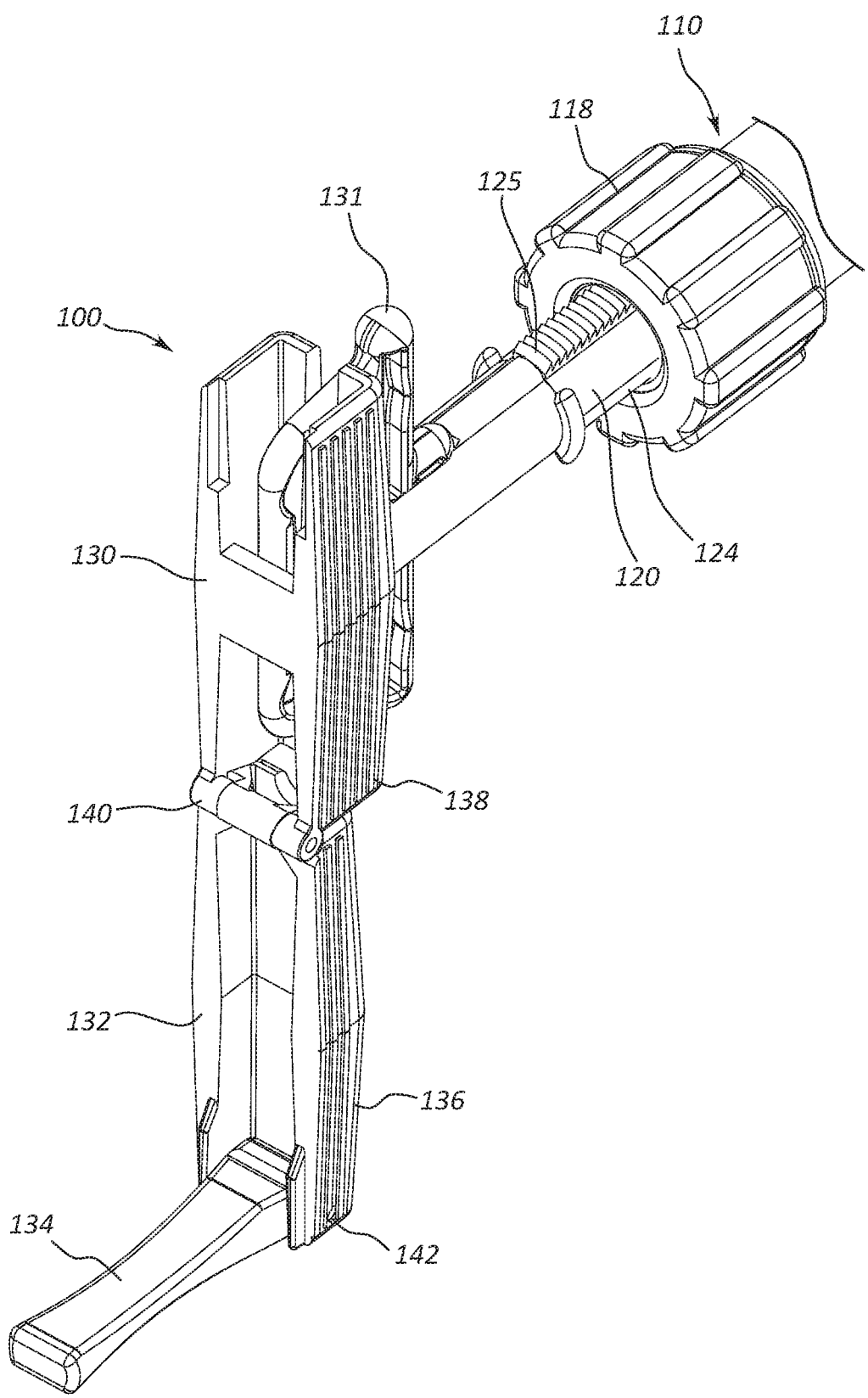
FIG. 1C is a partially cut-away perspective view of the inflation device of FIG. 1A, shown in a deployed state.
Figure 1D:
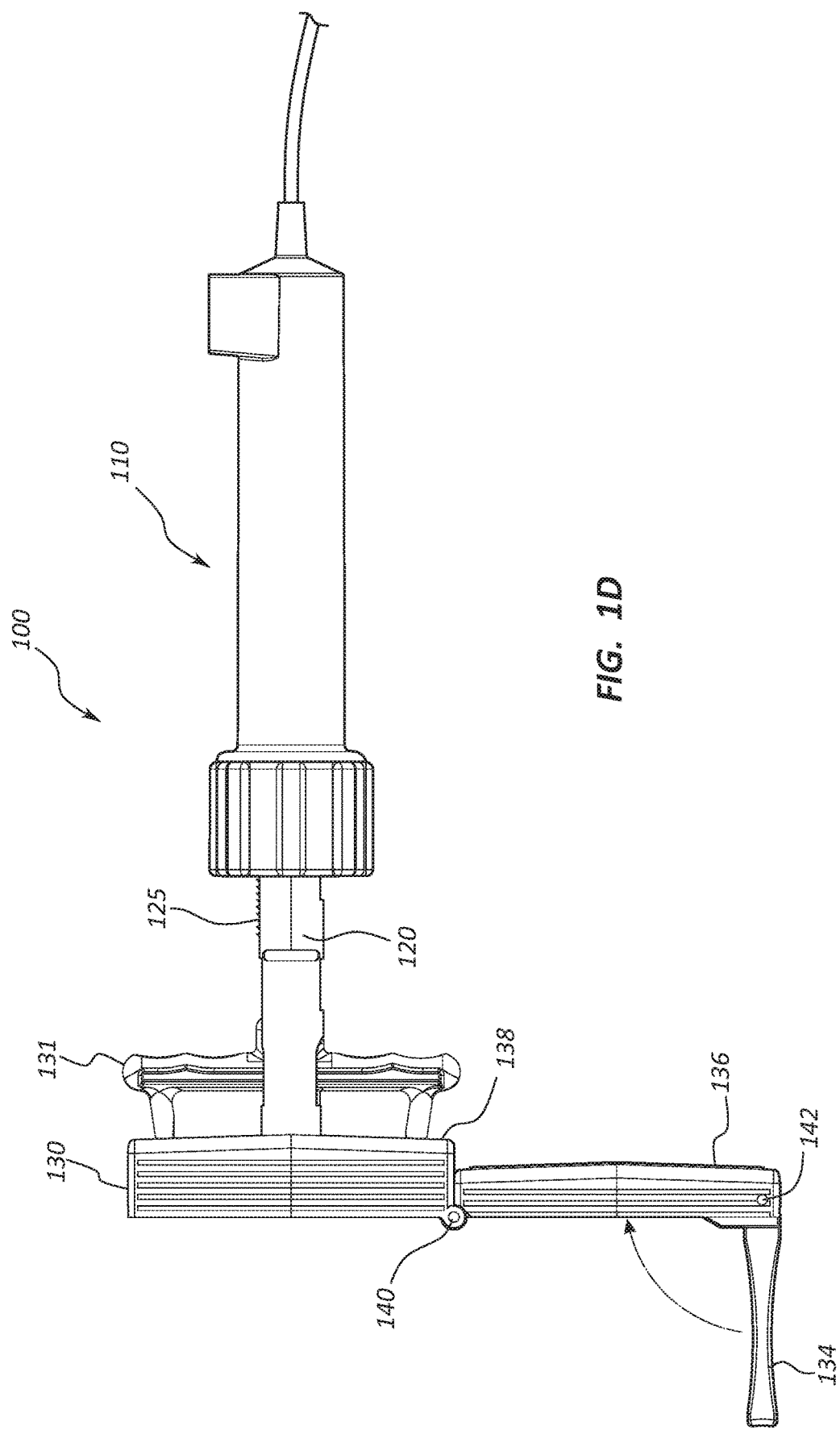
FIG. 1D is a side elevation view of the inflation device of FIG. 1A, shown in a deployed state.
Figure 1E:
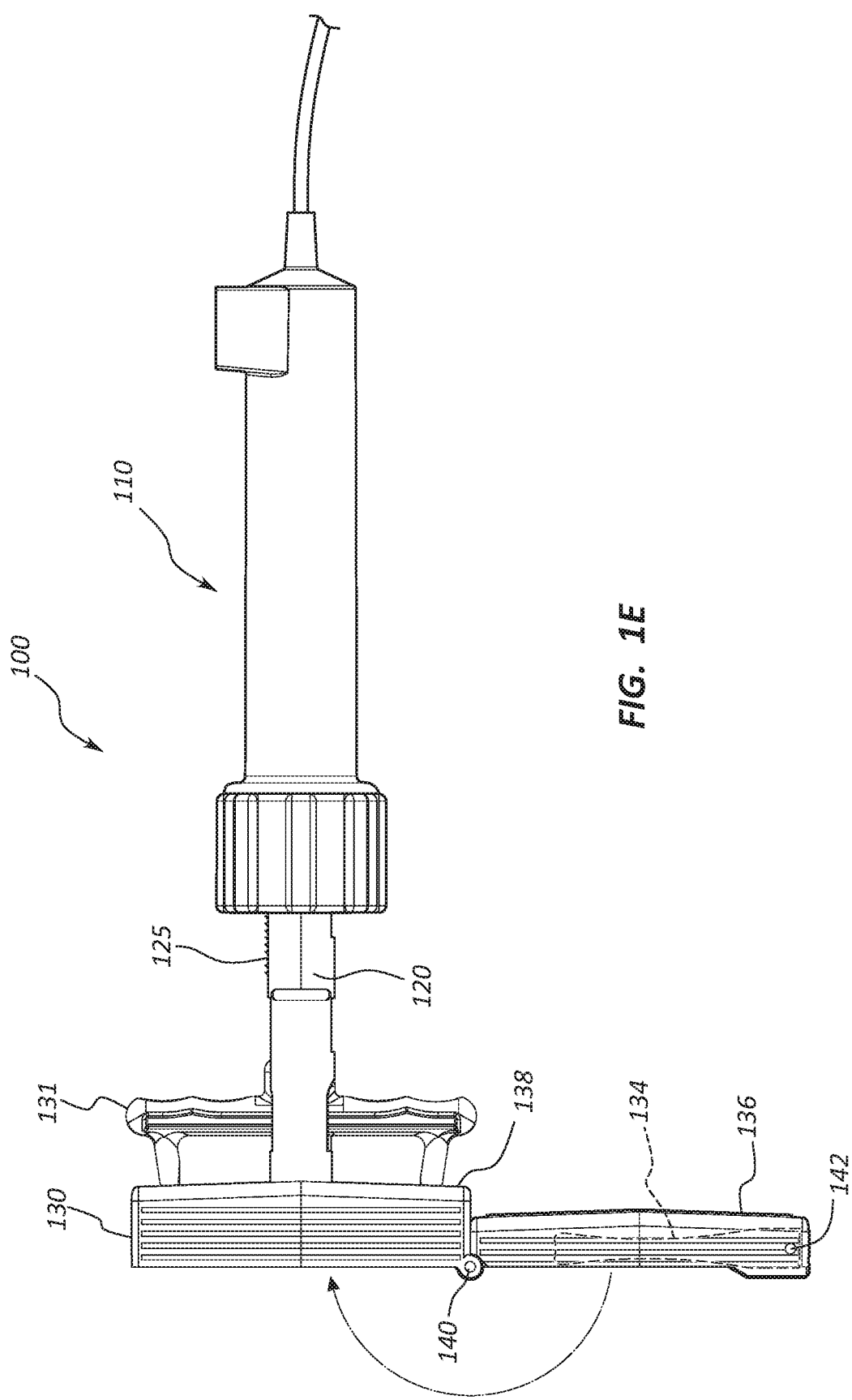
FIG. 1E is a second side elevation view of the inflation device of FIG. 1A, shown in a deployed state.
Figure 1F:
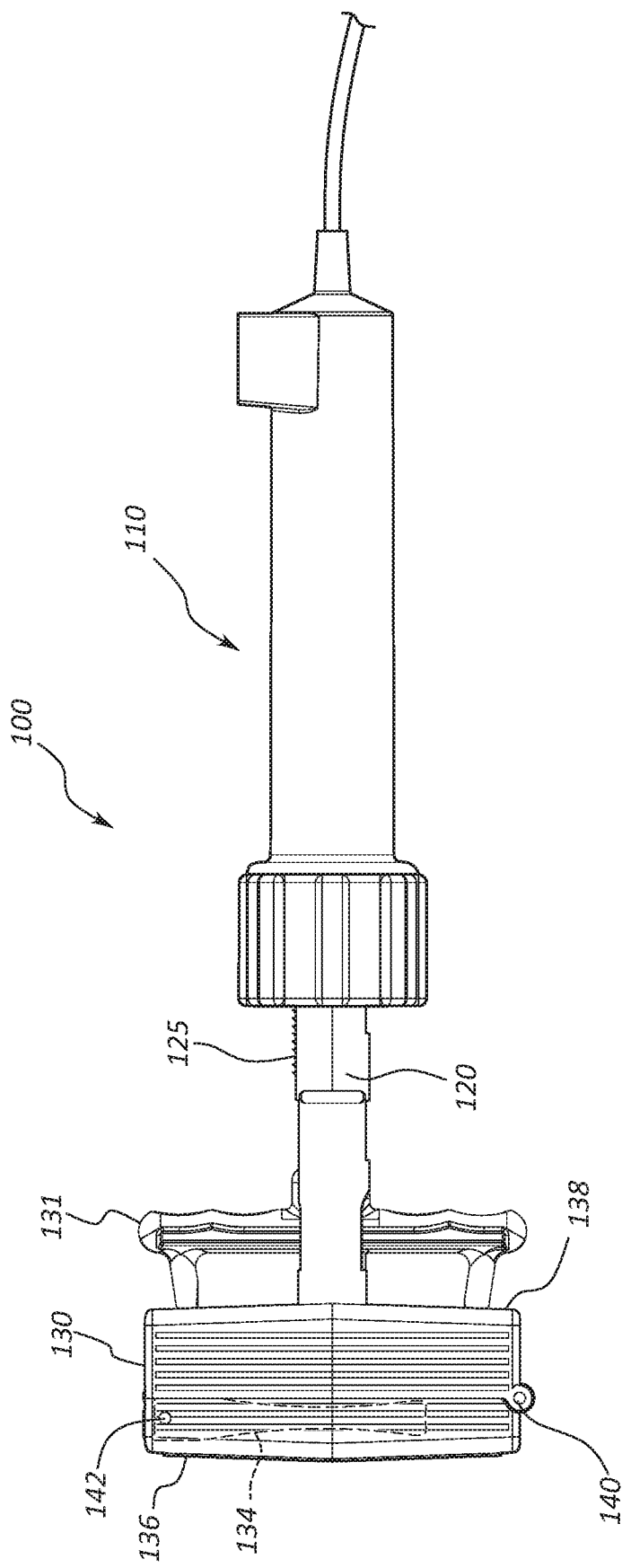
FIG. 1F is a side elevation view of the inflation device of FIG. 1A.
Figure 1H:
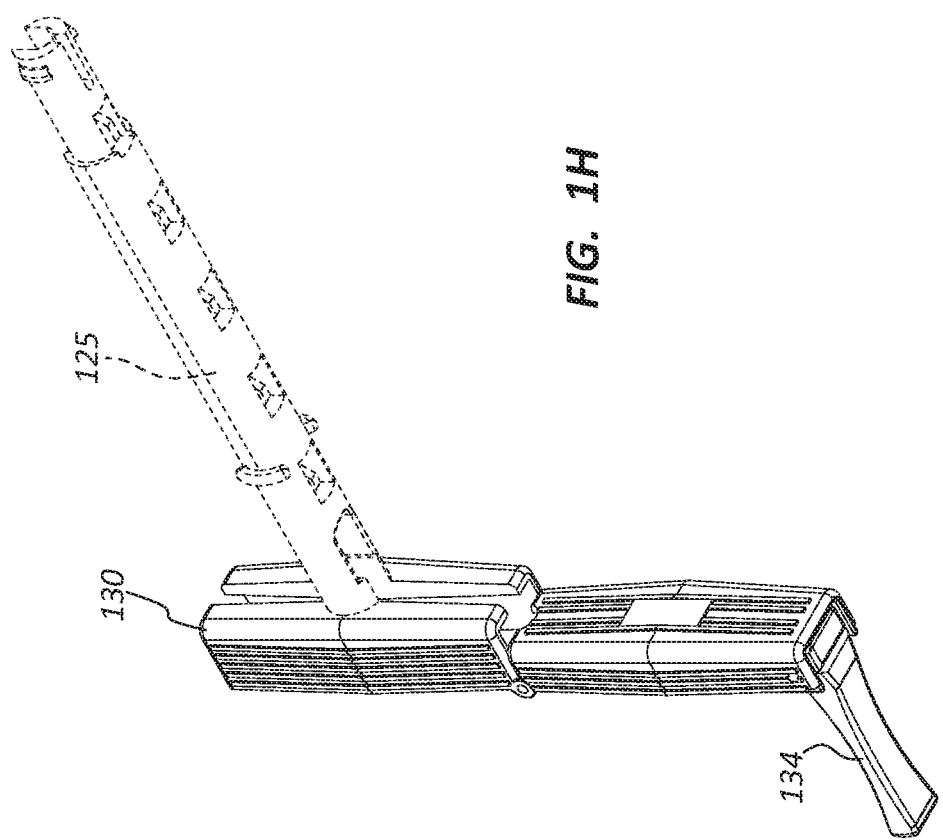
FIG. 1H is a second perspective view of the handle of the inflation device of FIG. 1A, shown in a deployed state.
Figure 1G:
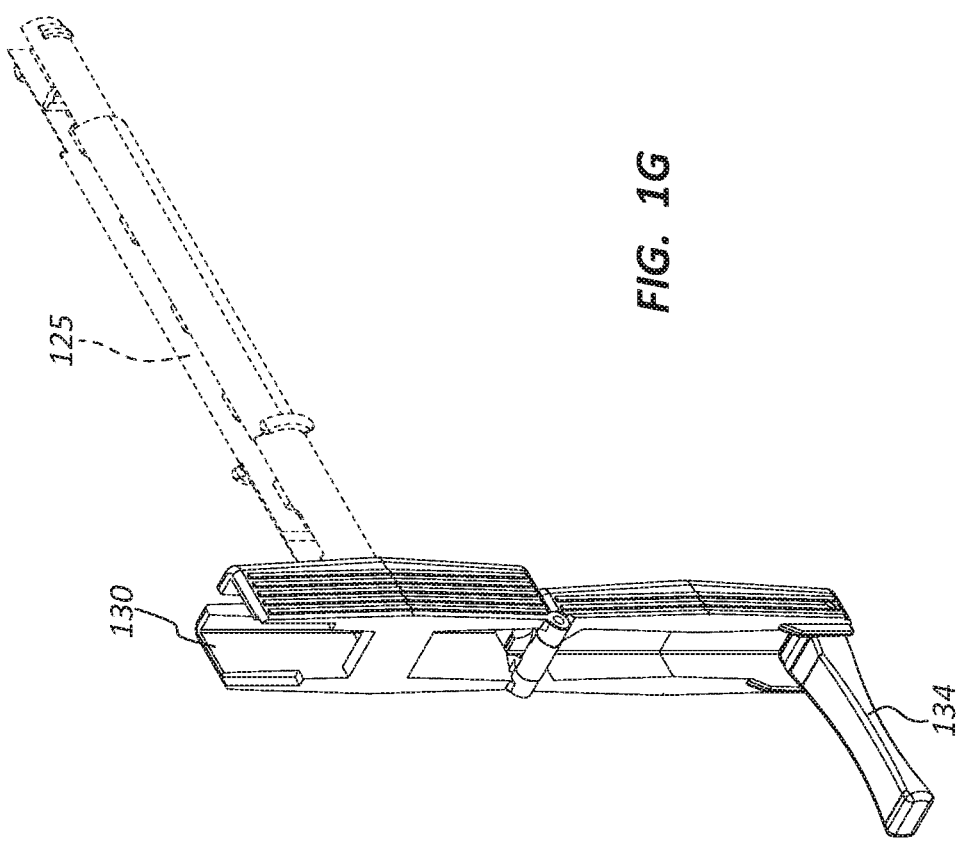
FIG. 1G is a first perspective view of the handle of the inflation device of FIG. 1A, shown in a deployed state.
Figure 2A:
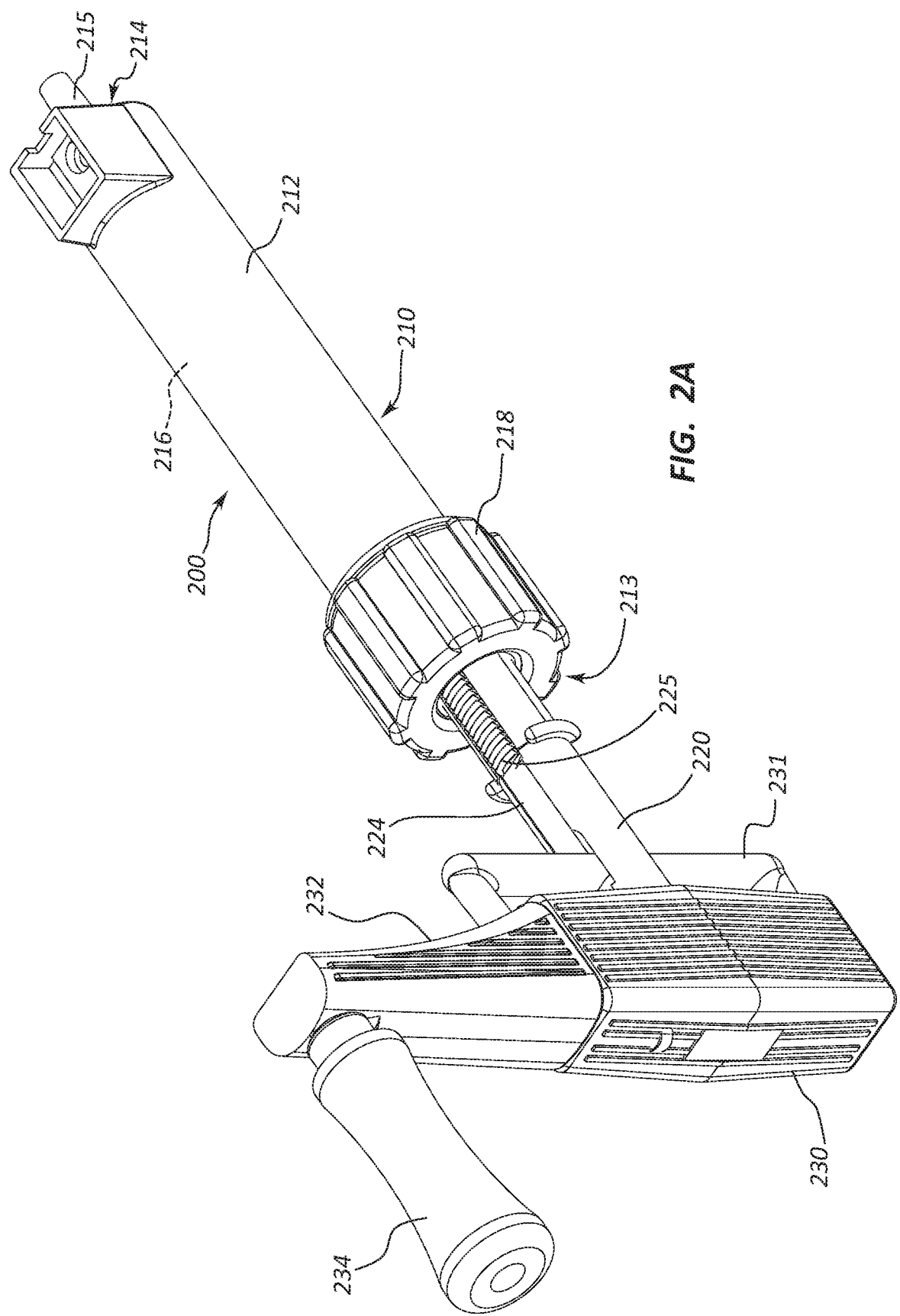
FIG. 2A is a perspective view of another inflation device assembly.
Figure 2B:
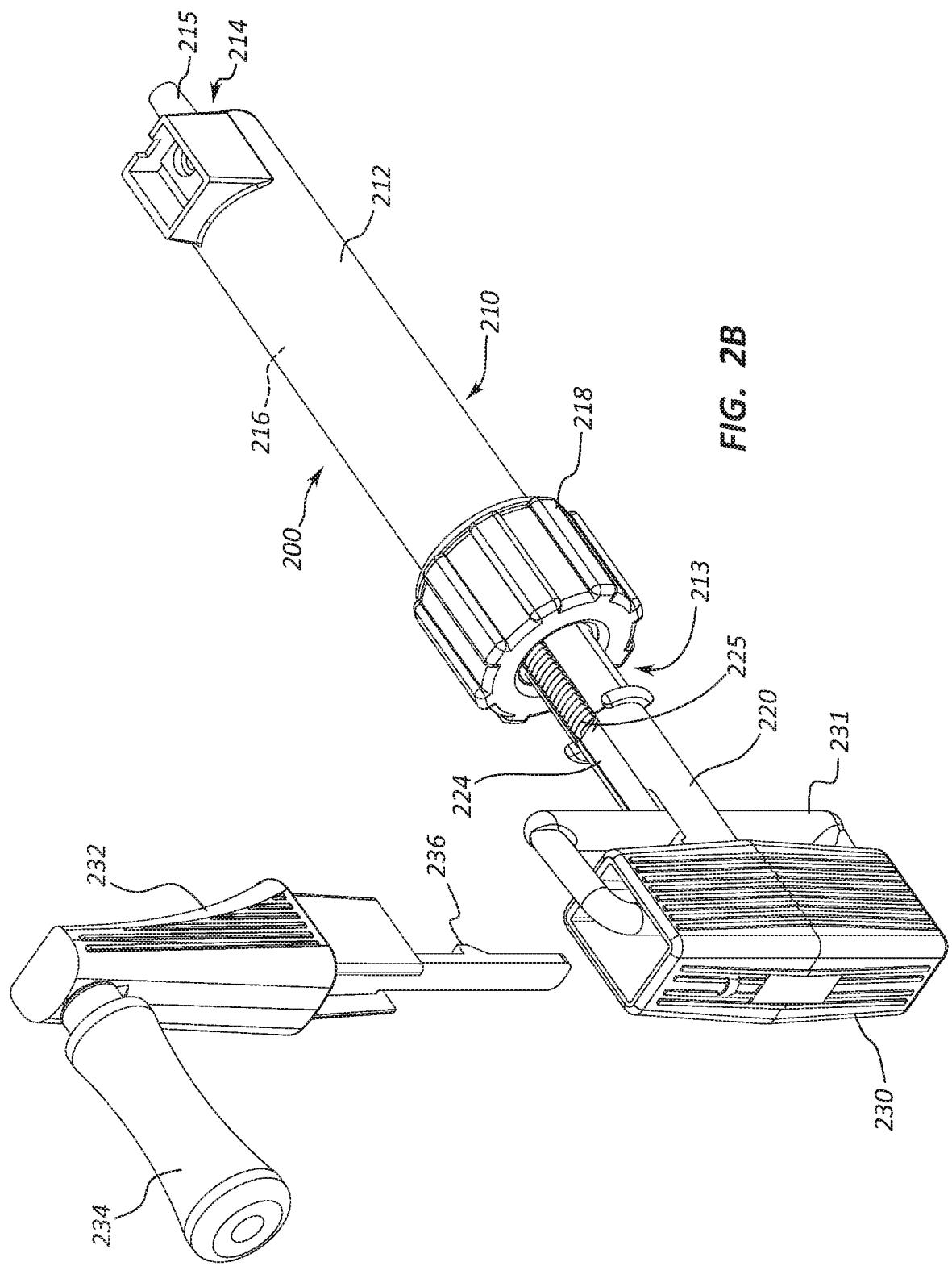
FIG. 2B is a perspective view of the inflation device assembly of FIG. 2A with a crank member detached from a handle.
Figure 2C:
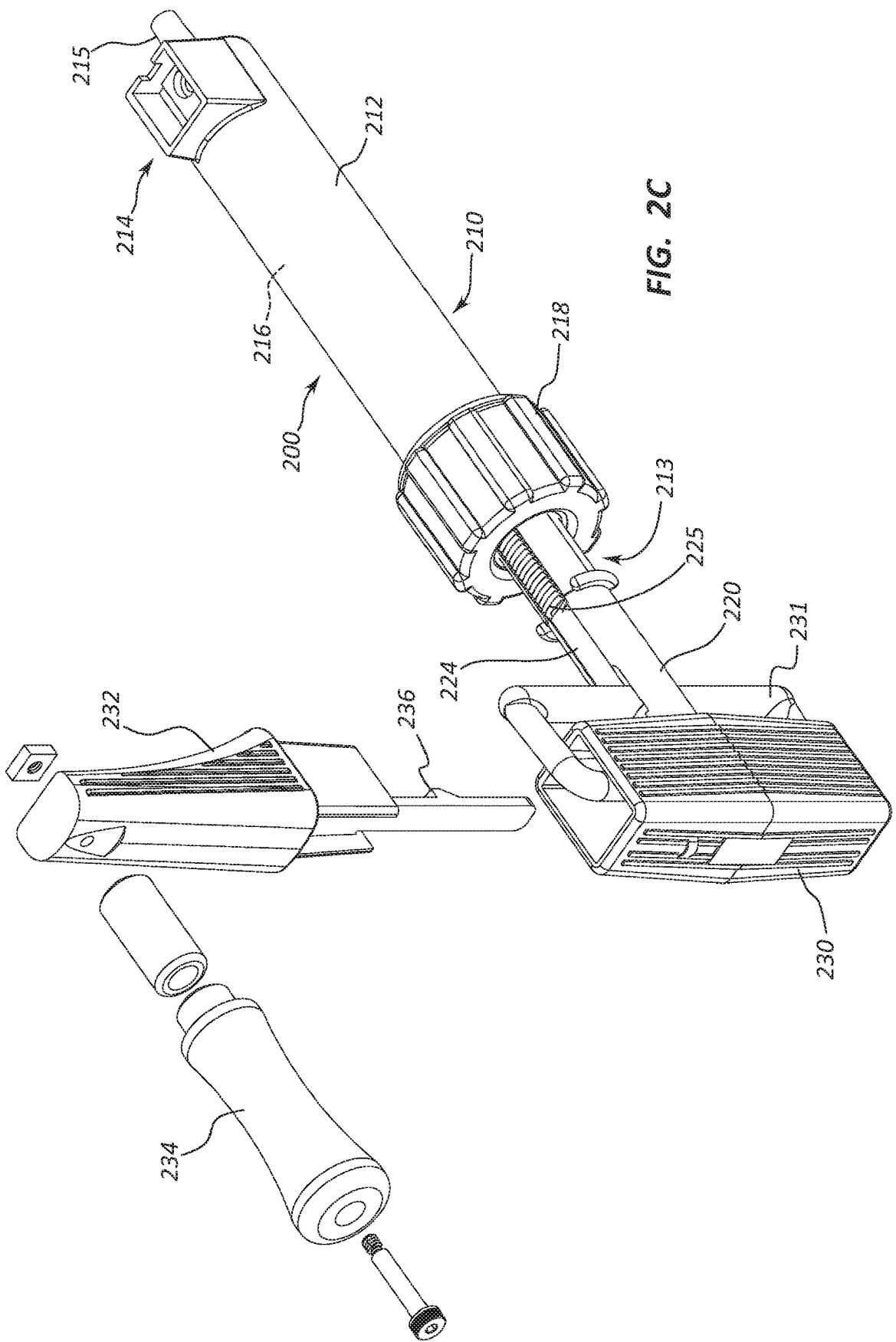
FIG. 2C is a perspective view of the inflation device assembly of FIG. 2A with a crank member detached from a handle in an exploded view.
Figure 2E:
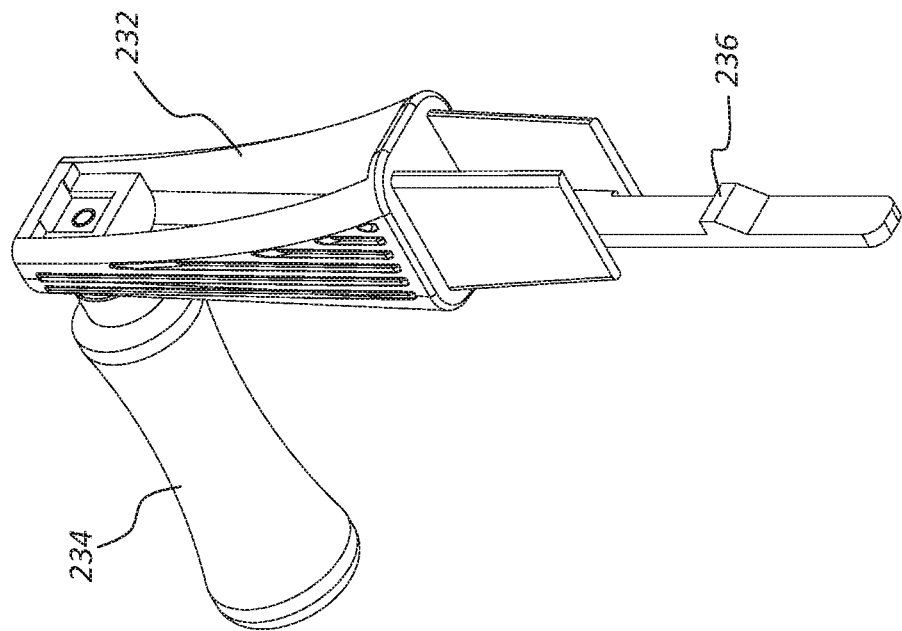
FIG. 2E is a second perspective view of the crank member of the inflation device assembly of FIG. 2A.
Figure 2D:
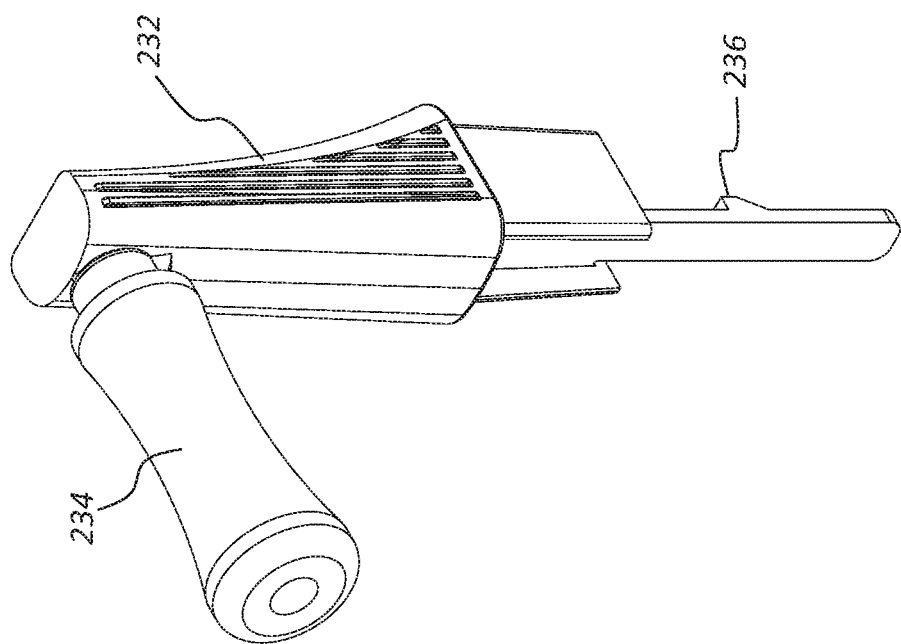
FIG. 2D is a first perspective view of the crank member of the inflation device assembly of FIG. 2A.
Figure 3A:
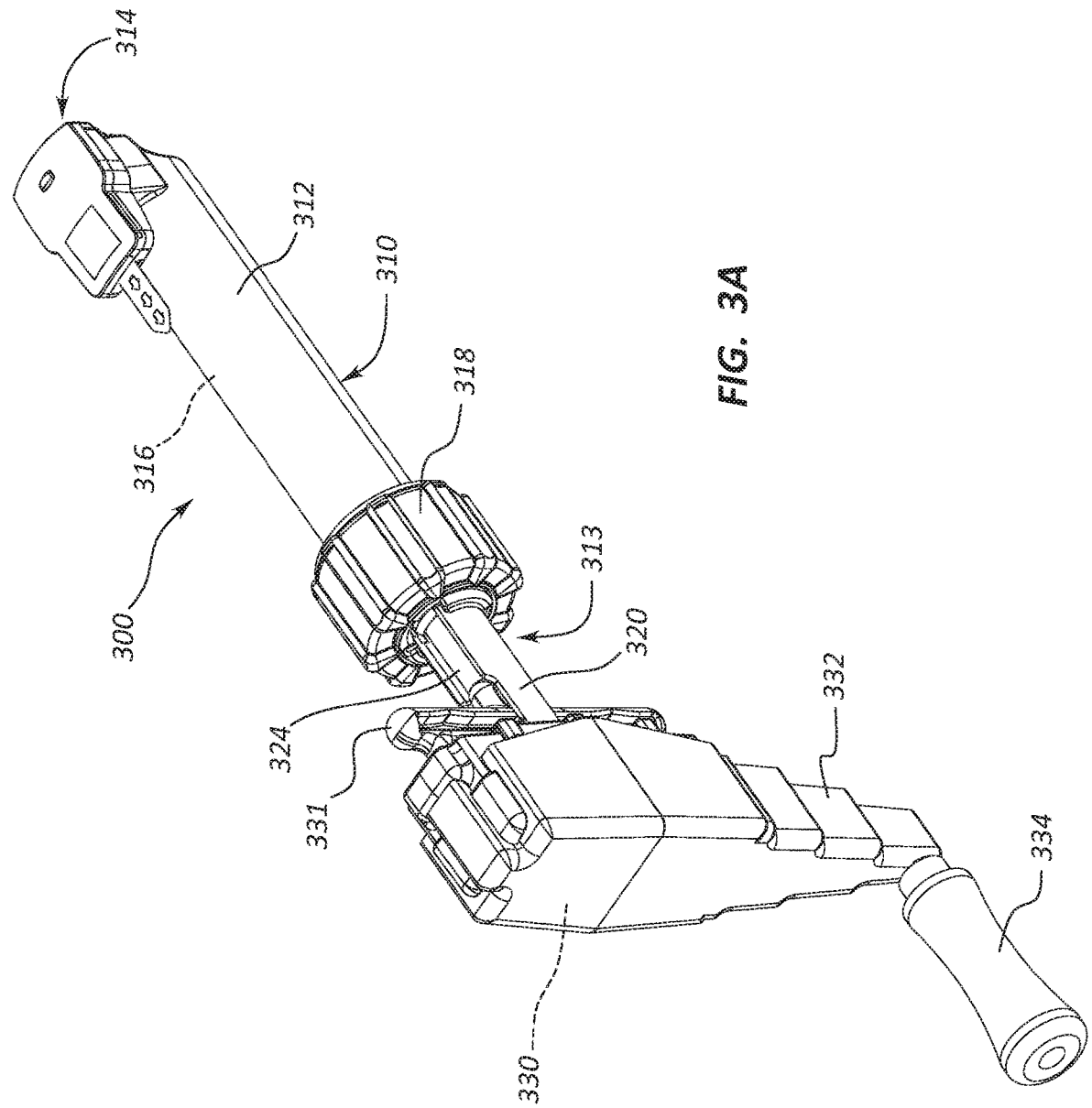
FIG. 3A is a perspective view of yet another inflation device assembly.
Figure 3B:
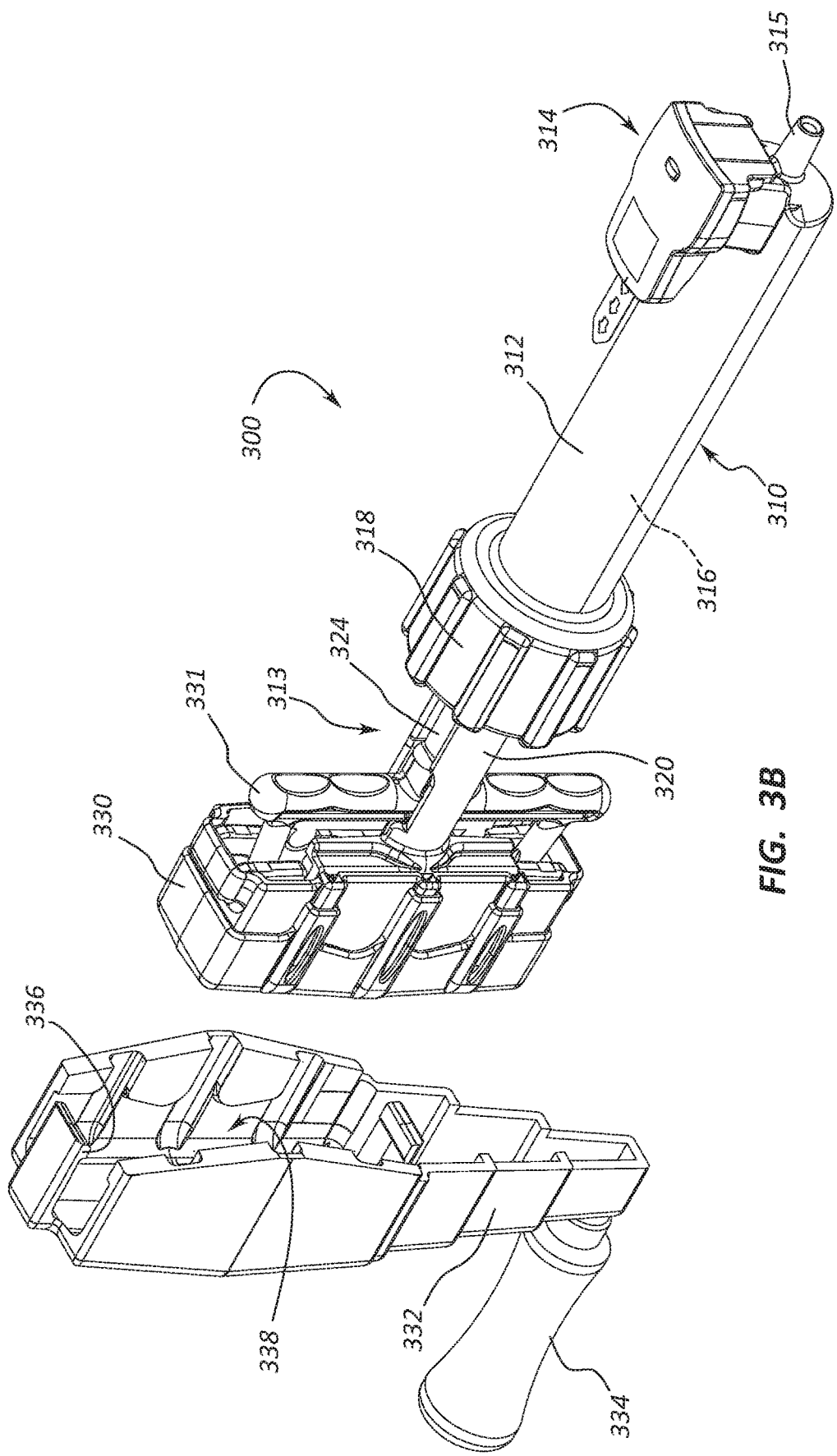
FIG. 3B is a perspective view of the inflation device assembly of FIG. 3A with a crank member detached from a handle.
Figure 3D:
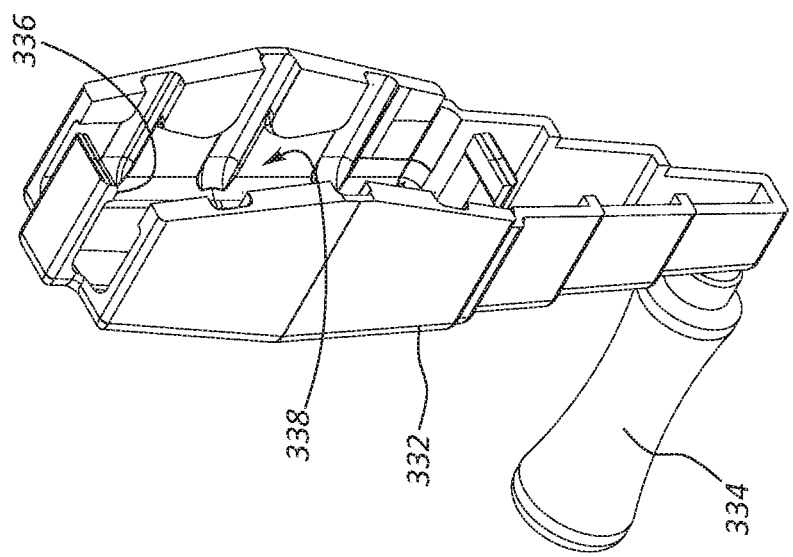
FIG. 3D is a second perspective view of the crank member of the inflation device assembly of FIG. 3A.
Figure 3C:
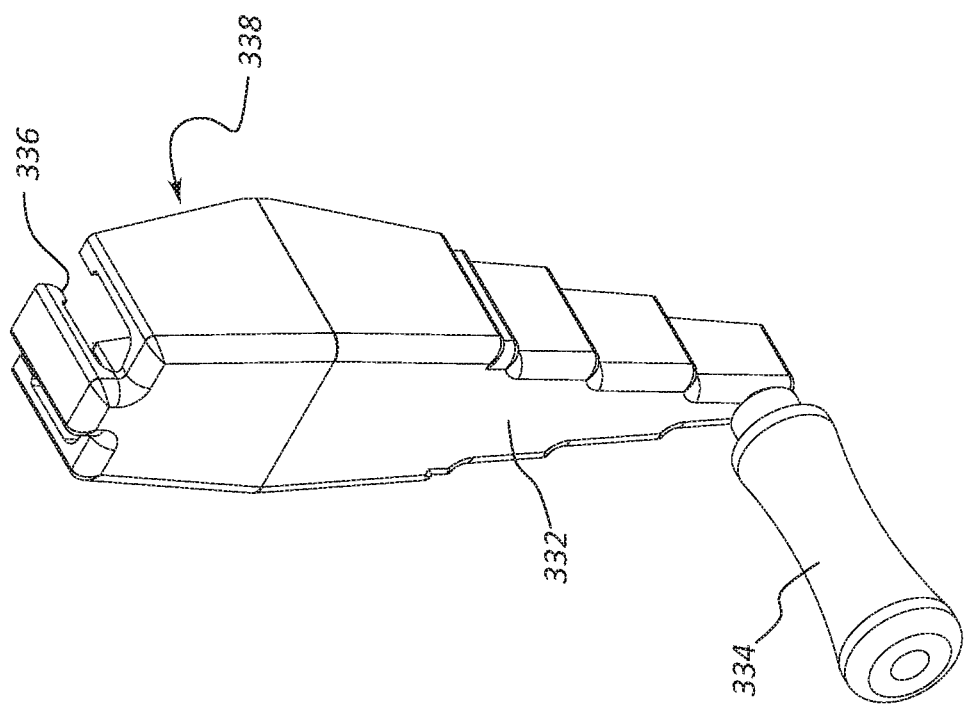
FIG. 3C is a first perspective view of the crank member of the inflation device assembly of FIG. 3A.
Figure 3H:
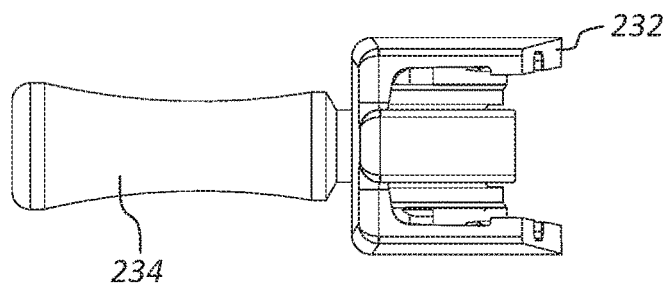
FIG. 3H is a front end view of the crank member of the inflation device assembly of FIG. 3A.
Figure 3F:
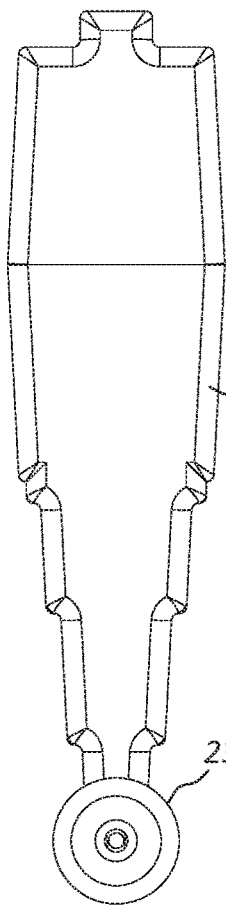
FIG. 3F is a top view of the crank member of the inflation device assembly of FIG. 3A.
Figure 3E:
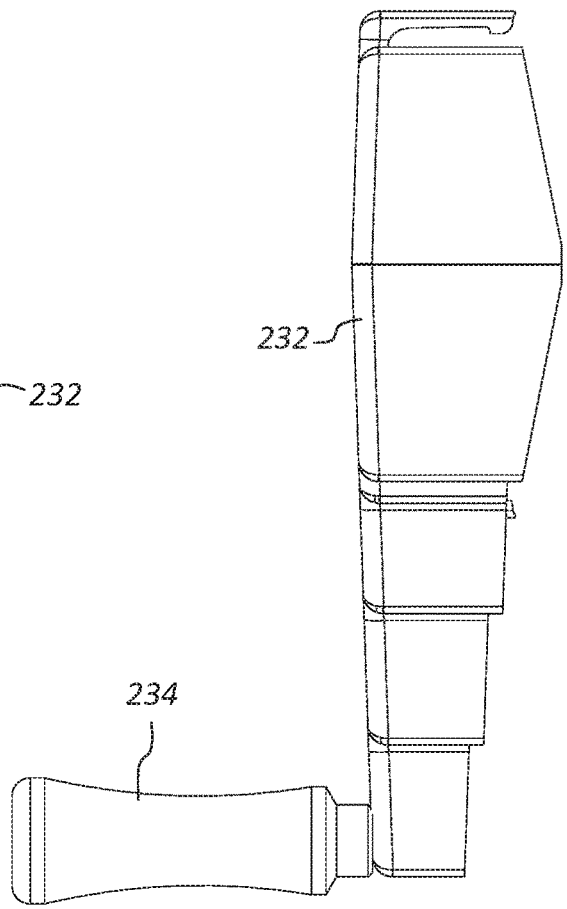
FIG. 3E is a side view of the crank member of the inflation device assembly of FIG. 3A.
Figure 3G:
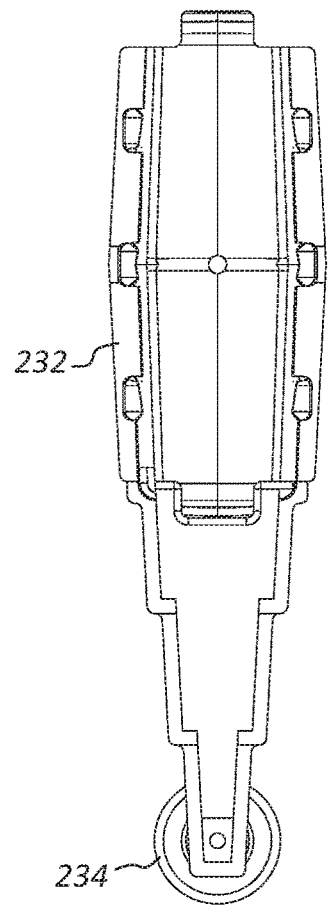
FIG. 3G is a bottom view of the crank member of the inflation device assembly of FIG. 3A.
Figure 3I:
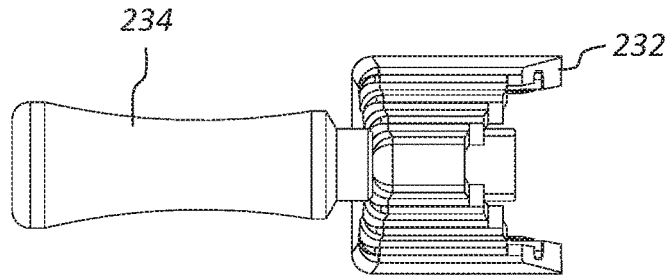
FIG. 3I is a back end view of the crank member of the inflation device assembly of FIG. 3A.
Figure 5A:
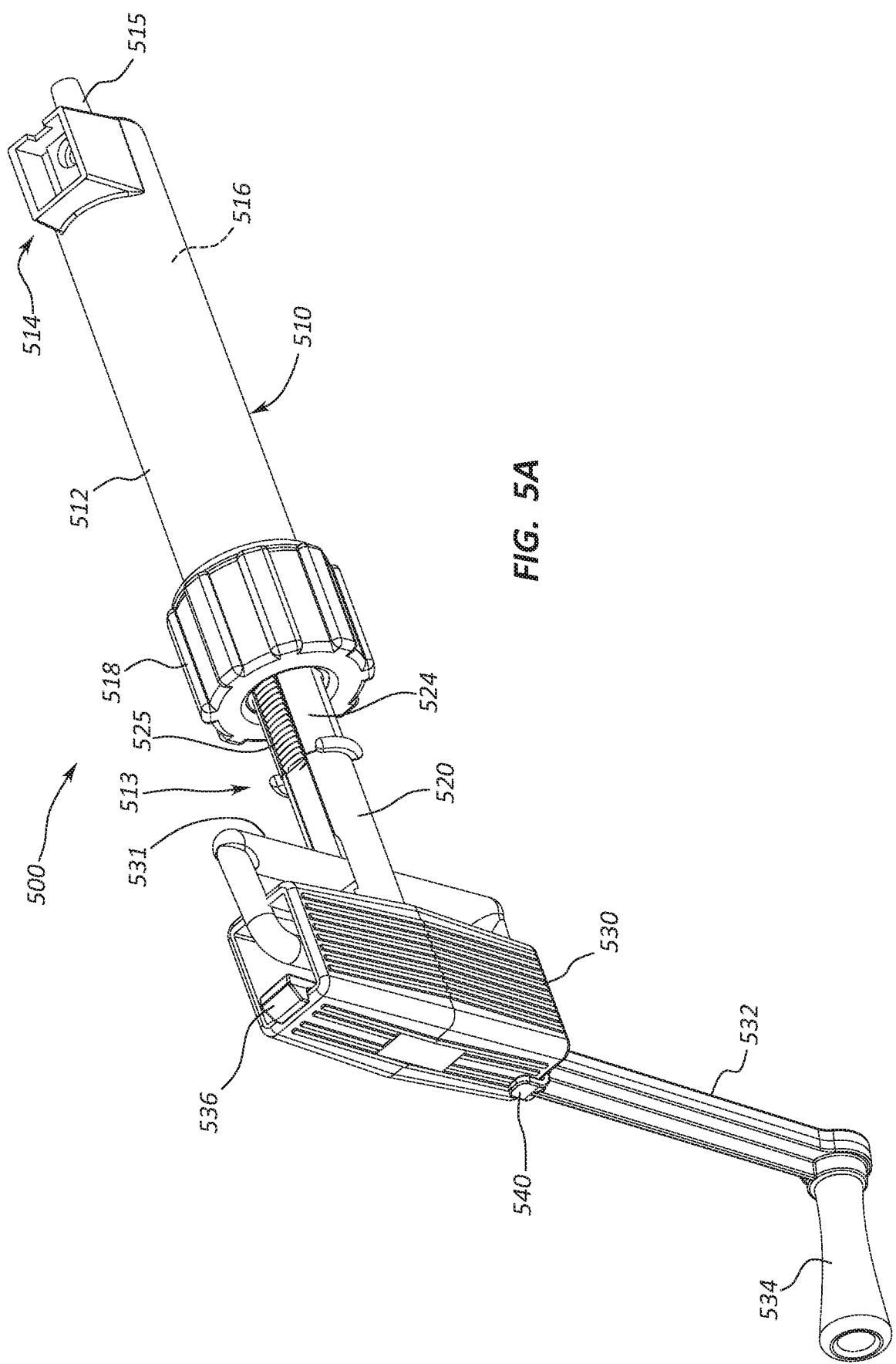
FIG. 5A is a perspective view of yet another inflation device assembly.

An inflation device may include a syringe which utilizes threads to advance or retract a plunger by rotating the plunger handle relative to the body of the syringe such that the threads cause longitudinal displacement of the plunger relative to the body. In some instances, an inflation syringe may further include retractable threads, enabling a practitioner to disengage the threads and displace the plunger by simply pushing or pulling the plunger.

The inflation syringe may comprise a coupling member configured to constrain movement of the plunger within the syringe body. The coupling member may comprise threads configured to engage with the retractable threads. Certain inflation devices include a mechanism in the handle of the device which allows the practitioner to disengage the threads through manipulating the mechanism. For example, in some instances the handle of such a device may include a "trigger" portion which may be configured to retract threads positioned on the plunger that were engaged with the coupling member when the trigger is actuated, thereby disengaging the threads from the coupling member.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the syringe portion of an inflation device, the proximal end of the syringe refers to the end nearest the handle and the distal end refers to the opposite end, the end nearest the inlet/outlet port of the syringe. Thus, if at one or more points in a procedure a practitioner changes the orientation of a syringe, as used herein, the term "proximal end" always refers to the handle end of the syringe (even if the distal end is temporarily closer to the practitioner).

"Fluid" is used in its broadest sense, to refer to any fluid, including both liquids and gases as well as solutions, compounds, suspensions, etc., which generally behave as fluids.

FIGS. 1A-7B illustrate different views of several inflation devices and related components. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIGS. 1A-1M depict one embodiment of an inflation device assembly 100. In the illustrated embodiment, the inflation device assembly 100 is partially comprised of a syringe 110. The inflation device assembly 100 includes three broad groups of components; each group may have numerous subcomponents and parts. The three broad component groups are: a body component such as syringe body 112, a pressurization component such as a plunger 120, and a handle 130.

The syringe body 112 may be formed of a generally cylindrical hollow tube configured to receive the plunger 120. The syringe body 112 may include an inlet/outlet port 115 located adjacent the a distal end 114 of the syringe body 112. In some embodiments, a coupling member 118 may be coupled to the syringe body 112 adjacent a proximal end 113 of the syringe body 112. The coupling member 118 may include a center aperture configured to allow the plunger 120 to pass through the coupling member 118 into the syringe body 112. Further, the coupling member 118 may include coupling member threads configured to selectively couple the coupling member 118 to the plunger 120. For example, the coupling member 118 may comprise a polymeric nut at the proximal end 113 of the syringe body 112.

The plunger 120 may be configured to be longitudinally displaceable within the syringe body 112. The plunger 120 may be comprised of a plunger shaft coupled to a plunger seal at the distal end of the plunger shaft. The plunger shaft may also be coupled to the handle 130 at the proximal end of the plunger shaft, with the plunger shaft spanning the distance between the plunger seal and the handle 130.

The handle 130 broadly refers to the group of components coupled to the proximal end of the plunger 120, some of which may be configured to be graspable by a user. In certain embodiments, the handle 130 may be configured such that the user may manipulate the position of the plunger 120 by manipulating the handle 130. Further, in some embodiments, the handle 130 may comprise an actuator mechanism configured to manipulate components of the inflation device assembly 100.

Any and every component disclosed in connection with any of the exemplary handle configurations herein may be optional. That is, though the handle 130 broadly refers to the components coupled to the proximal end of the plunger shaft which may be configured to be graspable by a user, use of the term "handle" is not meant to indicate that every disclosed handle component is always present. Rather, the term is used broadly, referring to the collection of components, but not specifically referring to or requiring the inclusion of any particular component, such as a crank member 132. Likewise, other broad groupings of components disclosed herein, such as the syringe 110 or the syringe body 112 and the plunger 120, may also refer to collections of individual subcomponents. Use of these terms should also be considered non-limiting, as each subcomponent may or may not be present in every embodiment.

Furthermore, the systems described herein may be configured for use with a crank member, such as the crank member 132, deployed and/or coupled in the system or with the crank member 132 in an undeployed or uncoupled state. In other words, systems within the scope of this disclosure may be configured to displace a plunger (through direct longitudinal displacement or through rotation of threads) with a crank handle undeployed or uncoupled to the system. Thus, the system may be configured such that a practitioner has the option of deploying or coupling a crank handle, or utilizing the system in a manner similar to conventional systems.

As shown in FIGS. 1A-1M, a fluid reservoir 116 may be defined by the space enclosed by the inside walls of the syringe body 112 between the plunger seal and the distal end 114 of the syringe body 112. Accordingly, movement of the plunger seal with respect to the syringe body 112 will alter the size and volume of the fluid reservoir 116.

As shown in FIGS. 1A-1M, in some embodiments, the syringe 110 may include a coupling member 118, fixedly coupled to the proximal end 113 of the syringe body 112. The coupling member 118 may utilize threads or other coupling mechanisms to fixedly couple the coupling member 118 to corresponding threads on the syringe body 112. Additionally, the coupling member 118 may engage external plunger threads 125 configured to couple the plunger 120 to the coupling member 118. The plunger 120 may thus be translated longitudinally with respect to the syringe body 112 by rotating the plunger 120 such that the interaction of the coupling member threads and the plunger threads 125 results in the longitudinal translation of the plunger 120. Such rotating motion may be achieved when a practitioner grasps the handle 130 and rotates it clockwise to extend the plunger 120 distally or counter-clockwise to retract the plunger 120 proximally.

Thus, when the plunger threads 125 and the coupling member threads are engaged, movement of the plunger 120 is constrained with respect to the syringe body 112, though the plunger 120 is not necessarily fixed with respect to the syringe body 112. For example, the plunger 120 may be rotatable, but not directly translatable, when the threads are engaged.

The plunger threads 125 may be configured such that they may be retracted within the plunger shaft. In some embodiments, the plunger threads 125 do not extend 360 degrees around the axis of the plunger shaft. For example, the plunger threads 125 may be formed on a thread rail 124 on the plunger shaft. The thread rail 124 may be retracted from the threads of the coupling member 118 by actuating a mechanism such as a trigger 131.

The retractable threads may allow a practitioner to displace the plunger shaft relative to the syringe body 112 either through rotation of the plunger shaft (and the subsequent interaction of threads), or by retracting the plunger threads 125 and displacing the plunger shaft by applying opposing forces on the plunger shaft and the syringe body 112. (The forces, of course, may move the plunger shaft distally or proximally with respect to the syringe body 112.) Both methods of displacement may be utilized during the course of a single therapy.

In some instances, a practitioner may desire to quickly displace the plunger shaft, for instance, while priming the inflation device assembly 100 or while priming or deflating an attached medical device such as a balloon. Quick displacement of the plunger shaft may be accomplished by retracting the plunger threads 125 and sliding the plunger shaft relative to the syringe body 112. For example, a practitioner may quickly fill the fluid reservoir 116 with fluid by disengaging the plunger threads 125 and pulling the plunger shaft in a proximal direction with respect to the syringe body 112. Further, a practitioner may quickly force fluid into lines leading to a medical device or quickly expel unwanted air bubbles from the fluid reservoir 116 by retracting the plunger threads 125 and repositioning the plunger shaft.

In other instances, the practitioner may desire more precise control over the position of the plunger shaft (for example when displacing the plunger shaft in order to adjust the fluid pressure or volume within the fluid reservoir 116) or it may simply be difficult to displace the plunger shaft due to high fluid pressure within the fluid reservoir 116. In these instances, the practitioner may opt to displace the plunger shaft by rotation of the plunger shaft.

When a practitioner rotates the handle 130 the plunger 120 is advanced distally or retracted proximally through the threaded engagement of the thread rail 124 and the coupling member 118. At high pressures, it can be difficult to rotate the handle 130 in order to increase the corresponding pressure in the balloon. In the embodiment depicted in FIGS. 1A-1M, the handle 130 comprises a crank member 132 that is extendable from the handle 130 in cantilevered fashion. The crank member 132 may further comprise a grip 134 for grasping by the practitioner's hand or fingers. The grip 134 is an optional component that, when present, is hingedly coupled to the crank member 132. Rotation of the handle 130 using the crank member 132 uses the mechanical advantage of leverage to further advance the plunger 120 at high internal pressures.

The crank member 132 and the grip 134 may be disposed in a deployed state for use and an undeployed state where it may be nested within the handle 130. In other words, the crank member 132 may be nested within the handle 130 and may be an integrated part of the handle 130. The crank member 132 may comprise a top portion 136 of the handle 130 and may be hingedly coupled to a bottom portion 138 of the handle 130. Once deployed, the crank member 132 is pivotable about a first hinge 140 and may extend radially from the longitudinal axis of the syringe 110 and the plunger 120. In some cases the crank member 132 may extend in a direction substantially perpendicular to the longitudinal axis of the syringe 110 and the plunger 120. The grip 134 may also be pivotable about a second hinge 142 to extend in a direction substantially parallel to (but radially offset from)

the longitudinal axis of the syringe 110 and the plunger 120 when the grip 134 is in a deployed state.

In the undeployed state, the grip 134 may be disposed within a channel or cavity of the crank member 132. The crank member 132 may function as the top portion 136 of the handle 130, effectively concealing the grip 134. This may thus allow the practitioner to selectively advance or retract the plunger 120 using the handle 130 without use of the crank member 132 when the crank member 132 is in the undeployed state (similar to conventional systems) or utilizing the mechanical advantage using the crank member 132 when the crank member 132 is in the deployed state.

The integrated crank member 132 allows a practitioner to use leverage in advancing the plunger 120 to achieve high pressures with the hand-held inflation device assembly 100, while also permitting disengagement of the thread rail 124 from the coupling member 118 to rapidly move the plunger 120 longitudinally within the syringe body 112 without being restricted to only rotational movement of the handle 130 to advance or retract the plunger 120. For example, once high inflation pressures are achieved in the inflation device assembly 100 using the crank member 132, deflation of the balloon can be achieved rapidly through actuating the trigger 131 to disengage the thread rail 124 and not requiring a cranking motion to retract the plunger 120.

In an alternative configuration, the crank member 132 is not hingedly coupled to the handle 130, but rather slidably coupled to the handle 130. In such a configuration, the top portion of the handle 130 slides laterally with respect to the bottom portion of the handle 130 (perpendicular to the longitudinal axis of the syringe body). The top portion is still maintained in communication with the remaining portion of the handle 130. Thus a radial extension of the handle 130 is provided which can provide a mechanical advantage when rotating the handle 130 via the crank member 132.

Additionally, the crank member 132 may be telescoping in nature having a selectable length depending upon the amount of mechanical advantage required for a given inflation routine.

Referring now to FIGS. 2A-2J, an inflation device assembly 200 is shown with a detachable crank member 232. Similar to the embodiment of FIGS. 1A-1M, the inflation device assembly 200 includes a syringe 210 comprising a syringe body 212 having a proximal end 213 and a distal end 214. A port 215 is disposed at the distal end 214 of the syringe body 212. The syringe body 212 further comprises a fluid reservoir 216. A coupling member 218 is disposed adjacent the proximal end 213 of the syringe body 212. The coupling member 218 is configured to engage a plunger 220 that extends within the syringe body 212. Engagement of the plunger 220 with the coupling member 218 may be accomplished by a releasably engagable thread rail 224 and plunger threads 225 as similarly described with the embodiment of FIGS. 1A-1M.

Adjacent the proximal end of the plunger 220 is located a handle 230 and trigger mechanism 231 for selectively engaging or disengaging the thread rail 224 with the coupling member 218. The handle 230 is further configured to permit a practitioner to rotatably displace the plunger 220 with respect to the coupling member 218, which in turn advances and/or retracts the plunger 220 within the fluid reservoir 216. Furthermore, the handle 230 is configured to permit a practitioner to longitudinally displace the plunger 220 with respect to the coupling member 218 without the need of rotational movement when the thread rail 224 and the plunger threads 225 are disengaged from the coupling member 218.

The crank member 232 is configured to releasably engage the handle 230, such that the crank member 232 extends laterally from the handle 230 (i.e., radially from the longitudinal axis of the plunger 220). In one embodiment the crank member 232 creates a snap fit within a channel or cavity that exists within the handle 230. In one example, the crank member 232 includes a ramped protrusion 236 that is configured to engage a shelf disposed within the handle 230 to allow a snap fit.

Alternatively, the crank member 232 may create an interference fit or is otherwise secured to the handle 230 to create a mechanical advantage when rotating the handle 230. The crank member 232 may optionally include a finger or hand grip 234 that may be rotatably coupled to the crank member 232 to provide an ergonomic interface for the practitioner.

Referring now to FIGS. 3A-3I, an inflation device assembly 300 is shown with a detachable crank member 332. Similar to the embodiment of FIGS. 1A-1M, the inflation device assembly 300 includes a syringe 310 comprising a syringe body 312 having a proximal end 313 and a distal end 314. A port 315 is disposed at the distal end 314 of the syringe body 312. The syringe body 312 further comprises a fluid reservoir 316. A coupling member 318 is disposed adjacent the proximal end 313 of the syringe body 312. The coupling member 318 is configured to engage a plunger 320 that extends within the syringe body 312. Engagement of the plunger 320 with the coupling member 318 may be accomplished by a releasably engagable thread rail 324 as similarly described with the embodiment of FIGS. 1A-1M.

Adjacent the proximal end of the plunger 320 is located a handle 330 and a trigger mechanism 331 for selectively engaging or disengaging the thread rail 324 with the coupling member 318. The handle 330 is further configured to permit a practitioner to rotatably displace the plunger 320 with respect to the coupling member 318, which in turn advances and/or retracts the plunger 320 within the fluid reservoir 316. Furthermore, the handle 330 is configured to permit a practitioner to longitudinally displace the plunger 320 with respect to the coupling member 318 without the need of rotational movement when the thread rail 324 and the plunger threads 325 are disengaged from the coupling member 318.

The handle 330 and the trigger mechanism 331 of the embodiment shown in FIGS. 3A-3I may include an internal lever system to provide a mechanical advantage in engaging and disengaging the thread rail 324 from the coupling member 318. Any configuration for providing mechanical advantage in operation of an inflation device, such as the configurations disclosed in U.S. Patent Publication Nos. 2013/0123693 and 2015/0051543, the contents of which are incorporated herein by reference in their entireties, may be used with the inflation devices disclosed herein, with the aid of the present disclosure.

A handle configured to provide a mechanical advantage when retracting a thread rail may be desirable for certain therapies that require large syringes or high pressure. Such therapies may also require a larger biasing force due to the size of the device or the pressure within the device. A handle providing a mechanical advantage may make devices configured for such therapies easier to use.

The crank member 332 is configured to releasably engage the handle 330, such that a portion of the crank member 332 extends laterally from the handle 330 (i.e., radially from the longitudinal axis of the plunger 320). In one embodiment, the crank member 332 creates a snap fit with the handle 330. This snap fit may optionally be achieved through a ramped protrusion 336 that is configured to engage a ledge disposed on one side the handle 330 to allow a snap fit. The crank member 332 may include a receiving cavity 338 to receive the body of the handle 330 to thus mate with and releasably engage the handle 330.

Alternatively, the crank member 332 may create an interference fit or is otherwise secured to the handle 330 to create a mechanical advantage when rotating the handle 330. The crank member 332 may optionally include a finger or hand grip 334 that may be rotatably coupled to the crank member 332 to provide an ergonomic interface for the practitioner.

Referring now to FIGS. 4A-4H, an inflation device assembly 400 is shown with an engagable crank member 432. Similar to the embodiment of FIGS. 1A-1M, the inflation device assembly 400 includes a syringe 410 comprising a syringe body 412 having a proximal end 413 and a distal end 414. A port 415 is disposed at the distal end 414 of the syringe body 412. The syringe body 412 further comprises a fluid reservoir 416. A coupling member 418 is disposed adjacent the proximal end 413 of the syringe body 412. The coupling member 418 is configured to engage a plunger 420 that extends within the syringe body 412. Engagement of the plunger 420 with the coupling member 418 may be accomplished by a releasably engagable thread rail 424 and plunger threads 425 as similarly described with the embodiment of FIGS. 1A-1M.

Adjacent the proximal end of the plunger 420 is located a handle 430 and a trigger mechanism 431 for selectively engaging or disengaging the thread rail 424 with the coupling member 418. The handle 430 is further configured to permit a practitioner to rotatably displace the plunger 420 with respect to the coupling member 418, which in turn advances and/or retracts the plunger 420 within the fluid reservoir 416. Furthermore, the handle 430 is configured to permit a practitioner to longitudinally displace the plunger 420 with respect to the coupling member 418 without the need of rotational movement when the thread rail 424 and the plunger threads 425 are disengaged from the coupling member 418.

The crank member 432 is configured to engage the base of the handle 430, such that a portion of the crank member 432 extends laterally from the handle 430 (i.e., radially from the longitudinal axis of the plunger 420). In one embodiment, the crank member 432 creates a snap fit with a post extending from the base of the handle 430. This snap fit may optionally be achieved through one or more ramped protrusions 436 that are configured to engage the base of the handle 430 (such as a post interconnecting the handle 430 to the plunger 420) to allow a snap fit. The crank member 432 may include a receiving channel 438 to receive and releasably engage the base of the handle 430. The crank member 432 may also include retaining flanges 440, which are configured to engage lateral members when rotated, such as the sides of the trigger mechanism 431.

Alternatively, the crank member 432 may create an interference fit or is otherwise secured to the handle 430 to create a mechanical advantage when rotating the handle 430. The crank member 432 may optionally include a finger or hand grip 434 that is optionally rotatably coupled to the crank member 432 to provide an ergonomic interface for the practitioner.

Referring now to FIGS. 5A-5I, an inflation device assembly 500 is shown with a detachable crank member 532. Similar to the embodiment of FIGS. 1A-1M, the inflation device assembly 500 includes a syringe 510 comprising a syringe body 512 having a proximal end 513 and a distal end 514. A port 515 is disposed at the distal end 514 of the syringe body 512. The syringe body 512 further comprises a fluid reservoir 516. A coupling member 518 is disposed adjacent the proximal end 513 of the syringe body 512. The coupling member 518 is configured to engage a plunger 520 that extends within the syringe body 512. Engagement of the plunger 520 with the coupling member 518 may be accomplished by a releasably engagable thread rail 524 and plunger threads 525 as similarly described with the embodiment of FIGS. 1A-1M.

Adjacent the proximal end of the plunger 520 is located a handle 530 and a trigger mechanism 531 for selectively engaging or disengaging the thread rail 524 with the coupling member 518. The handle 530 is further configured to permit a practitioner to rotatably displace the plunger 520 with respect to the coupling member 518, which in turn advances and/or retracts the plunger 520 within the fluid reservoir 516. Furthermore, the handle 530 is configured to permit a practitioner to longitudinally displace the plunger 520 with respect to the coupling member 518 without the need of rotational movement when the thread rail 524 and the plunger threads 525 are disengaged from the coupling member 518.

The crank member 532 is configured to releasably engage the handle 530, such that the crank member 532 extends laterally from the handle 530 (i.e., radially from the longitudinal axis of the plunger 520). In one embodiment the crank member 532 creates a snap fit within a channel or cavity that exists within the handle 530. In one example, the crank member 532 includes a ramped protrusion 536 that is configured to engage an edge of the handle 530 to allow a snap fit.

Alternatively, the crank member 532 may create an interference fit or is otherwise secured to the handle 530 to create a mechanical advantage when rotating the handle 530. The crank member 532 may optionally include a finger or hand grip 534 that is optionally rotatably coupled to the crank member 532 to provide an ergonomic interface for the practitioner.

Referring now to FIGS. 6A-6H, an inflation device assembly 600 is shown with a slidable crank member 632. Analogous to the embodiment of FIGS. 1A-1M, the inflation device assembly 600 includes a syringe 610 comprising a syringe body 612 having a proximal end 613 and distal end 614. A port 615 is disposed at the distal end 614 of the syringe body 612. The syringe body 612 further comprises a fluid reservoir 616. A coupling member 618 is disposed adjacent the proximal end 613 of the syringe body 612. The coupling member 618 is configured to engage a plunger 620 that extends within the syringe body 612. Engagement of the plunger 620 with the coupling member 618 may be accomplished by a releasably engagable thread rail 624 and plunger threads 625 analogous to that described in connection with the embodiment of FIGS. 1A-1M.

In the illustrated embodiment, a handle 630 and a trigger mechanism 631 for selectively engaging or disengaging the thread rail 624 with the coupling member 618 is disposed adjacent the proximal end of the plunger 620. The handle 630 may be further configured to permit a practitioner to rotatably displace the plunger 620 with respect to the coupling member 618, which in turn advances and/or retracts the plunger 620 within the fluid reservoir 616. Furthermore, the handle 630 is configured to permit a practitioner to longitudinally displace the plunger 620 with respect to the coupling member 618 without the need of rotational movement when the thread rail 624 and the plunger threads 625 are disengaged from the coupling member 618.

The crank member 632 of the illustrated embodiment is configured to slidably couple to the handle 630, such that the crank member 632 is nested within the handle 630 prior to deployment and extends laterally from the handle 630 (i.e., radially from the longitudinal axis of the plunger 620) when in a deployed state. In one embodiment, the crank member 632 comprises rails 650, a pull tab 651, and a finger or hand grip 634. The rails 650 slidably couple to the handle 630 such that the rails 650 are disposed within the handle 630 prior to deployment and laterally extend from the handle 630 when the crank member 632 is deployed. Rail stops 652 are disposed at the medial end of the rails 650 and are configured to engage the handle 630 when the crank member 632 is deployed to prevent the crank member 632 from being removed from the handle 630. The crank member 632 may engage a stationary portion of the plunger 620 within the handle 630 such that the trigger mechanism 631 is not inadvertently activated to disengage the plunger threads 625 from the coupling member 618 when the crank member 632 is used to rotate the handle 630. An inadvertent disengagement of the plunger threads 625 from the coupling member 618 may result in a sudden loss of pressure within the fluid reservoir 616 and a coupled device such as a balloon.

A pull tab 651 may be disposed at the lateral end of the crank member 632. A hinge 642 may be configured to pivotably couple the pull tab 651 to the rails 650. The pull tab 651 may be configured to be graspable by the practitioner to facilitate deployment of the crank member 632. Prior to deployment of the crank member 632, the pull tab 651 may be aligned with the longitudinal axis of the crank member 632 and disposed outside of the handle 630. The practitioner may grasp the pull tab 651 and displace the crank member 632 laterally from the handle 630 until the rail stops 652 engage with the handle 630.

The finger or hand grip 634 may be configured to provide an ergonomic interface with the crank member 632 for the practitioner to facilitate rotation of the handle 630. The grip 634 may be generally rectangular in cross-section such that it may be nested between the rails 650 prior to deployment of the crank member 632. The grip 634 may comprise grip enhancing features such as recesses, bumps, texturing, soft material covering, etc. The grip 634 may be fixedly coupled to the pull tab 651 such that when the pull tab 651 is pivoted from a position in alignment with the longitudinal axis of the crank member 632 to a non-aligned position, the grip 634 may be elevated from between the rails 650 such that it may be graspable by the practitioner. The pull tab 651 may be configured to frictionally interfere with the lateral ends of the rails 650 when pivoted to prevent the grip 634 from freely falling back into a nested position. The grip 634 may rotate relative to the pull tab 651 as the crank member 632 is rotated by the practitioner such that the practitioner does not ungrasp and re-grasp the grip 634 as the crank member 632 is rotated.

Figures 6A, 6B:
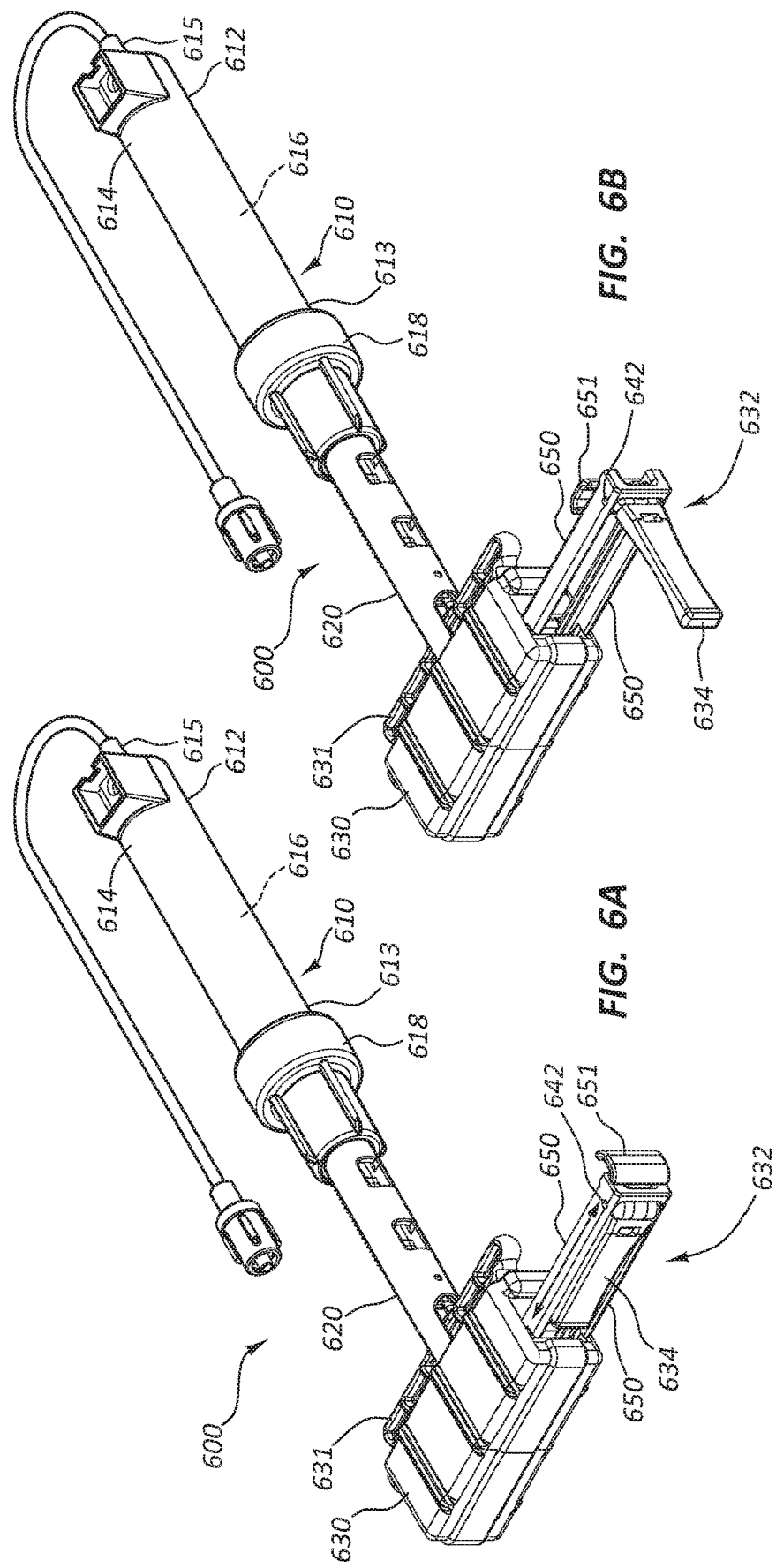
FIG. 6A is a perspective view of another inflation device assembly.
FIG. 6B is a perspective view of the inflation device assembly of FIG. 6A with the crank member in a deployed state.
Figure 6E:
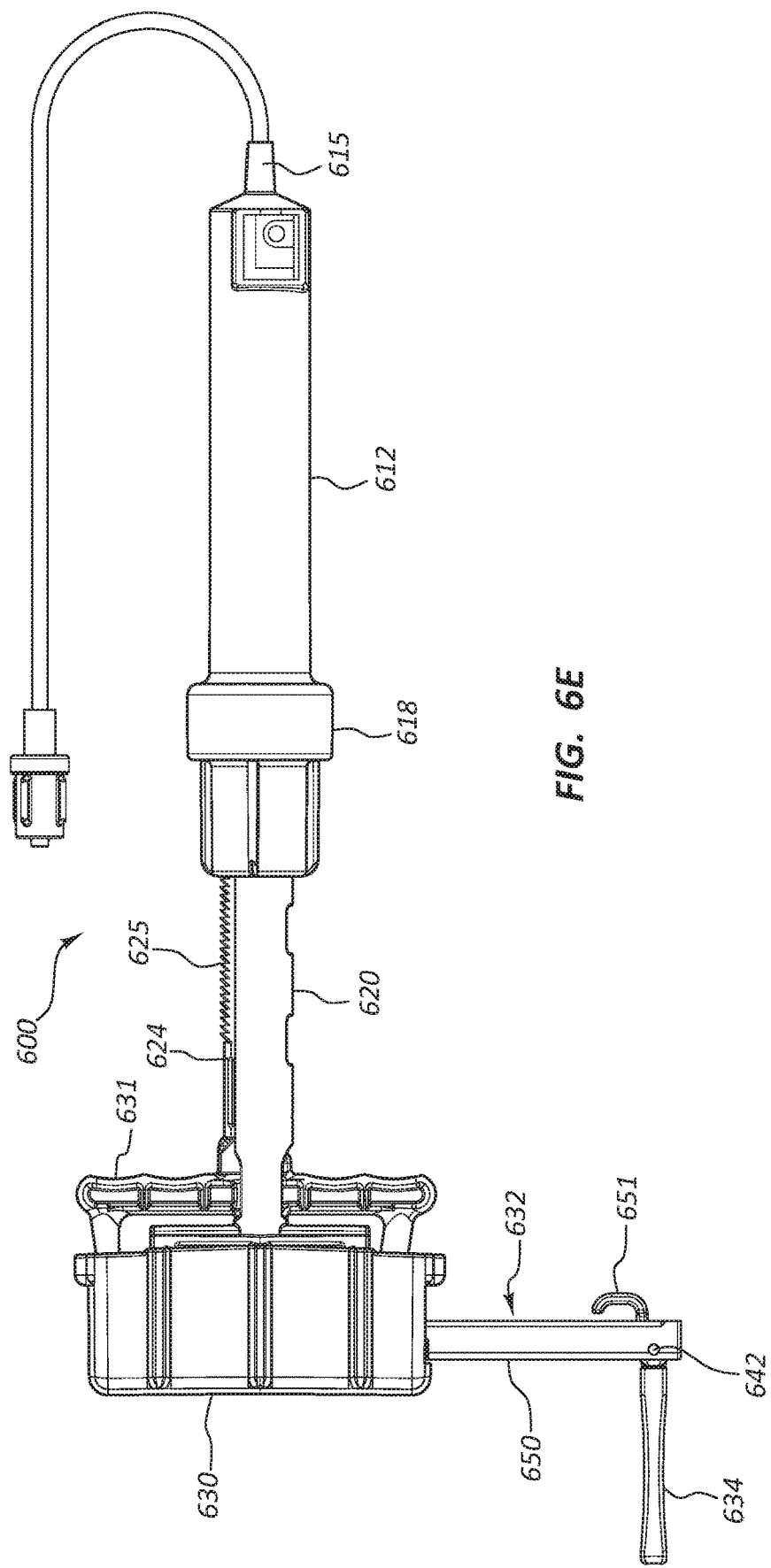
FIG. 6E is a side view of the inflation device of FIG. 6A in the deployed state of FIG. 6B.
Figure 6H:
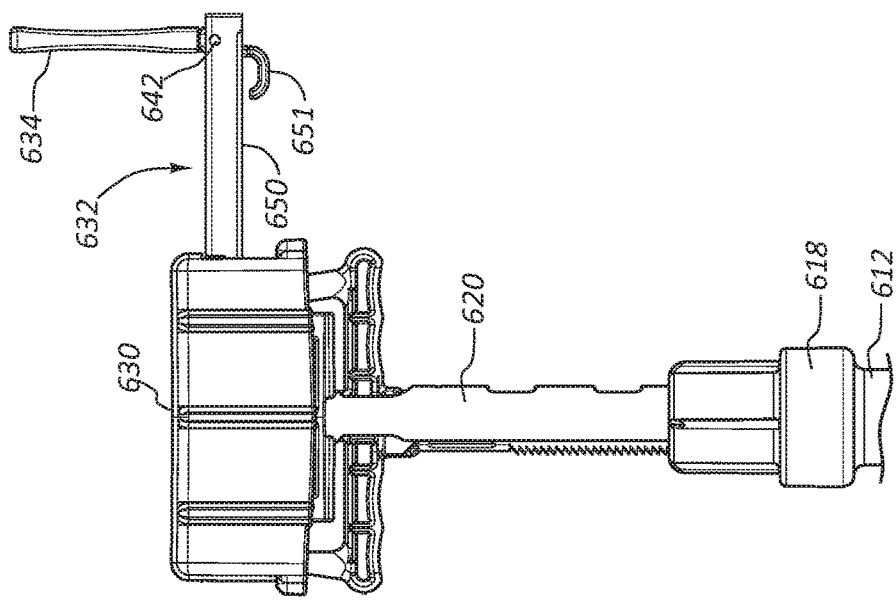
FIG. 6H is a side view of a portion of the inflation device assembly of FIG. 6A with the crank member in a fully deployed state.
Figure 6G:
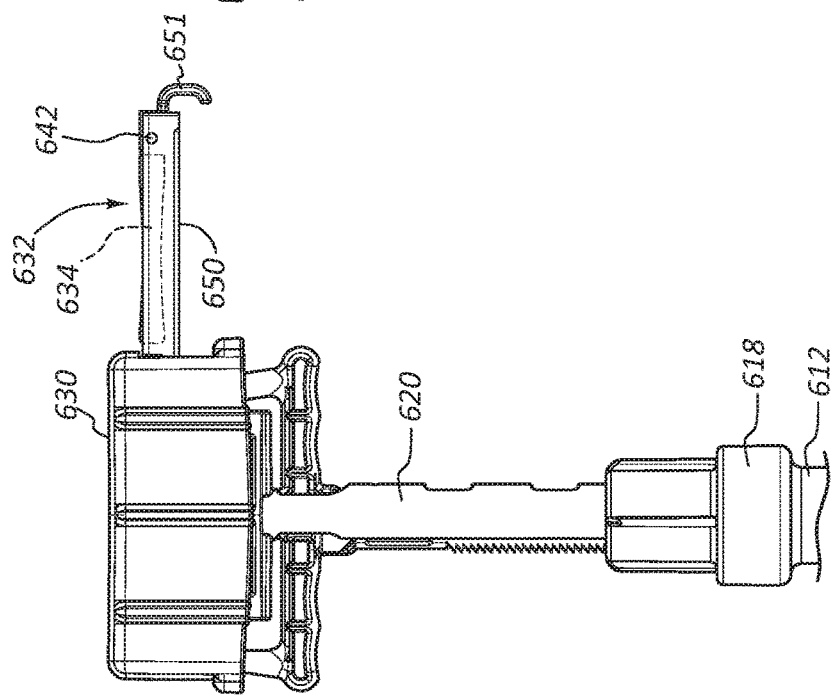
FIG. 6G is a side view of a portion of the inflation device assembly of FIG. 6A with the crank member in a partially deployed state.
Figure 6F:
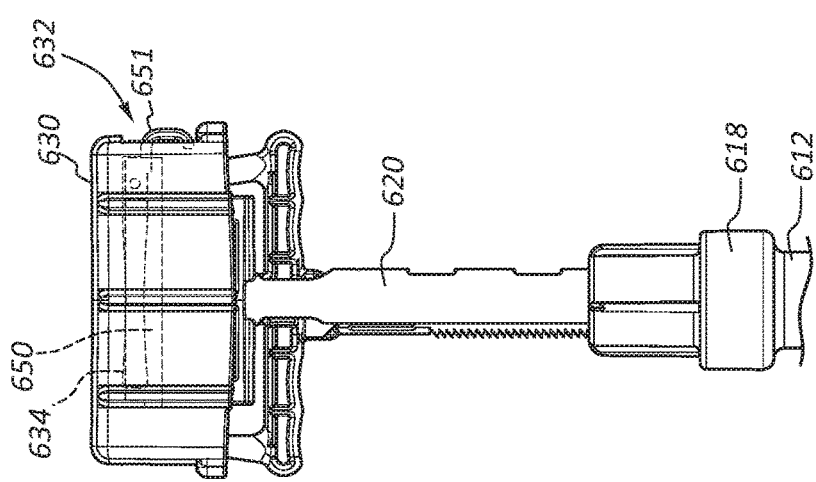
FIG. 6F is a side view of a portion of the inflation device assembly of FIG. 6A.

Referring to FIGS. 6F-6H, a portion of the inflation device assembly 600 is shown. FIG. 6F shows the inflation device assembly 600 prior to deployment of the crank member 632 with the crank member 632 disposed within the handle 630 and the pull tab 651 disposed at the exterior of the handle 630. FIG. 6G shows the inflation device assembly 600 with the crank member 632 in a partially deployed state such that the crank member 632 extends laterally from the handle 630, the pull tab 651 is disposed in alignment with the longitudinal axis of the crank member 632, and the grip 634 is nested between the rails 650. FIG. 6H shows a portion of the inflation device assembly 600 with the crank member 632 fully deployed such that the crank member 632 extends laterally from the handle 630, the pull tab 651 is pivoted out of alignment with the longitudinal axis of the crank member 632, and the grip 634 is elevated to a vertical orientation.

In use the inflation devices and assemblies described above may be pressurized using any of the following steps or actions, each of which may be optional or interchanged. An inflation device is obtained which comprises a syringe body, a plunger within the syringe body, a handle coupled to the plunger (such as through a thread rail coupled to a coupling member) and a crank member coupled to the handle. The crank member may be deployed from a nested position in the handle prior to rotation of the crank member. Alternatively, the crank member may be releasably engaged with the handle with a snap fit prior to rotation of the crank member.

The plunger may be advanced by grasping the syringe body in one hand and rotating the crank member clockwise (as viewed from the proximal end) with the other hand. Before rotation of the crank member, the thread rail of the plunger may be disengaged from the syringe body (or coupling member). The plunger may be advanced through longitudinal movement of the handle to a first internal pressure. Then the thread rail may be re-engaged to the syringe body after reaching the first internal pressure. The plunger may be further advanced through rotational movement of the handle via the crank member to achieve a second pressure. After the therapy is complete or when desirous of depressurizing the syringe, the thread rail can be disengaged from the syringe body and retracted through longitudinal movement of the handle.

Figure 7A:
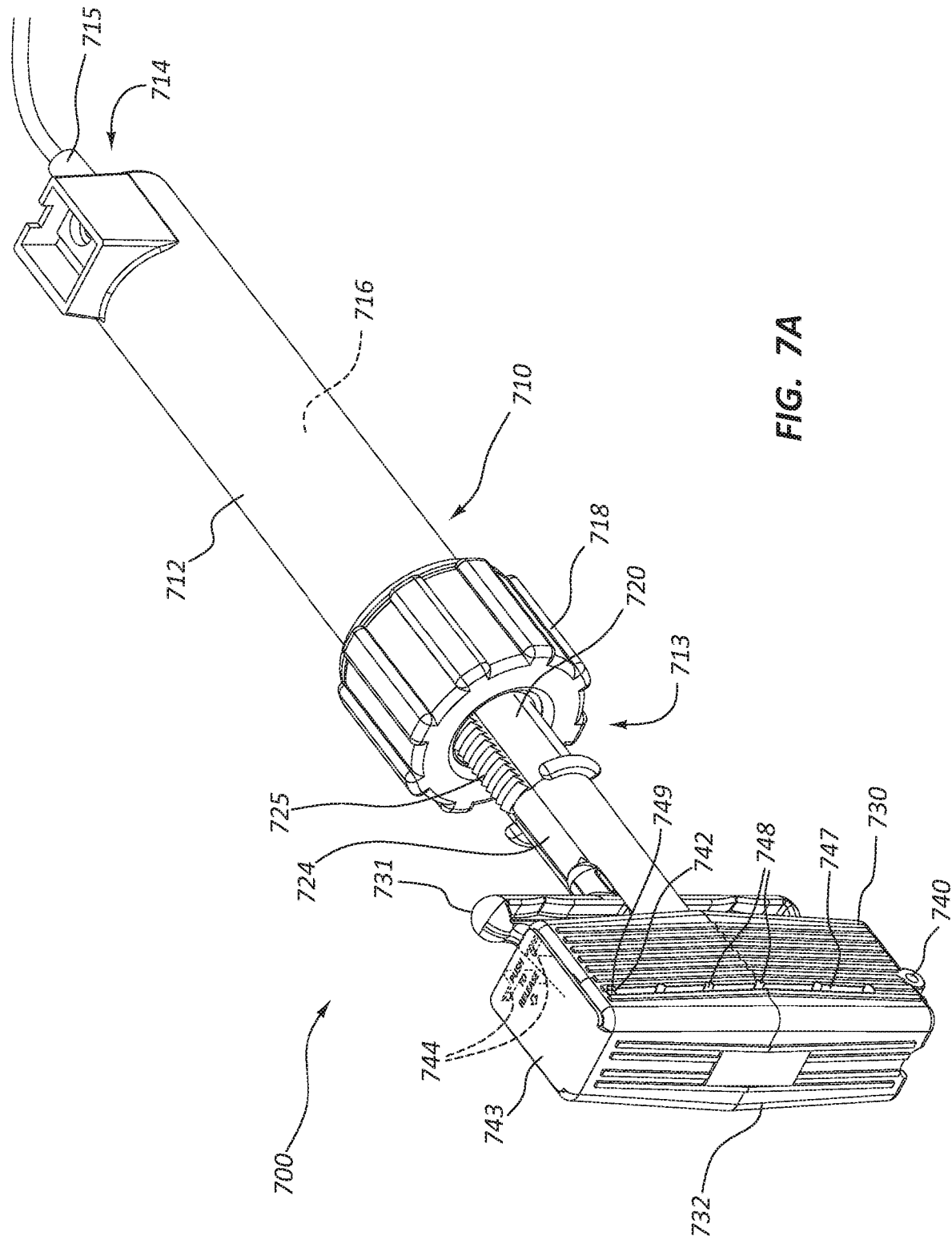
FIG. 7A is a perspective view of another inflation device assembly.
Figure 7B:
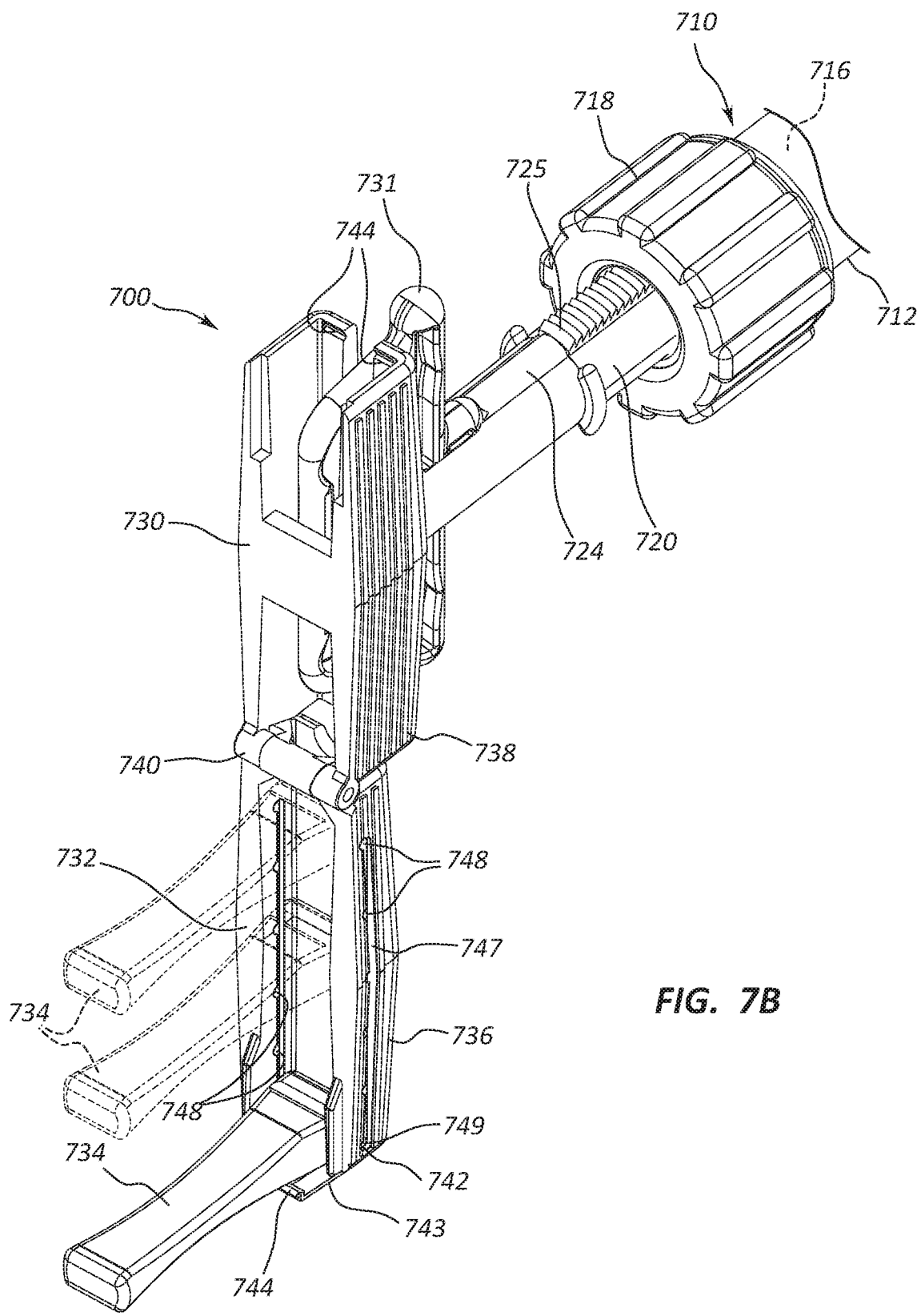
FIG. 7B is a perspective view of a portion of the inflation device assembly of FIG. 7A with the crank member in a fully deployed state.

Referring now to FIGS. 7A-7B, an inflation device assembly 700 is shown with a rotatable crank member 732. Analogous to the embodiment of FIGS. 1A-1M, the inflation device assembly 700 includes a syringe 710 comprising a syringe body 712 having a proximal end 713 and a distal end 714. A port 715 is disposed at the distal end 714 of the syringe body 712. The syringe body 712 further comprises a fluid reservoir 716. A coupling member 718 is disposed adjacent the proximal end 713 of the syringe body 712. The coupling member 718 is configured to engage a plunger 720 that extends within the syringe body 712. Engagement of the plunger 720 with the coupling member 718 may be accomplished by a releasably engagable thread rail 724 and plunger threads 725 analogous to that described in connection with the embodiment of FIGS. 1A-1M.

In the illustrated embodiment, a handle 730 and a trigger mechanism 731 for selectively engaging or disengaging the thread rail 724 with the coupling member 718 is disposed adjacent the proximal end of the plunger 720. The handle 730 may be further configured to permit a practitioner to rotatably displace the plunger 720 with respect to the coupling member 718, which in turn advances and/or retracts the plunger 720 within the fluid reservoir 716. Furthermore, in the illustrated embodiment, the handle 730 is configured to permit a practitioner to longitudinally displace the plunger 720 with respect to the coupling member 718 without the need of rotational movement when the thread rail 724 and the plunger threads 725 are disengaged from the coupling member 718.

In some instances, the practitioner may desire precise control over the position of the plunger 720 (for example when displacing the plunger 720 in order to adjust the fluid pressure or volume within the fluid reservoir 716). It also may be difficult, i.e. require extensive manual force, to displace the plunger 720 due to high fluid pressure within the fluid reservoir 716. There may also be incidents where a large volume of high pressure fluid must be delivered requiring several rotations of the handle 730. In such cases rotation of the handle 730 may be a significant source of hand fatigue as the practitioner would need to ungrasp and re-grasp the handle 730 for each 180 degrees of rotation. Hence, certain therapies may include use of an inflation device assembly 700 in conditions where neither direct longitudinal displacement of the plunger 720 or direct rotation of the handle 730 are ergonomically optimal for the practitioner.

As noted, above, when a practitioner rotates the handle 730, the plunger 720 is advanced distally or retracted proximally through the threaded engagement of the thread rail 724 and the coupling member 718. At high pressures, it can be difficult to rotate the handle 730 via rotation of the practitioner's wrist in order to deliver high pressure fluid to a balloon or other medical device, as the pressure within the inflation device results in a force resisting rotation of the handle 730 to further increase pressure. In some elements analogous to other embodiments described herein, the embodiment depicted in FIGS. 7A and 7B, the handle 730 comprises a crank member 732 that is hingedly coupled to the handle 730, such that it may be extendible in cantilevered fashion. The crank member 732 may comprise a grip 734 for grasping by the practitioner's hand or fingers. The grip 734 may be hingedly coupled to the crank member 732. The grip 734 may be rotatably coupled to the crank member 732 such that the grip 734 can rotate about its longitudinal axis. Rotation of the handle 730 using the crank member 732 utilizes the mechanical advantage of leverage—due to the radial offset between the deployed grip 734 and the axis of rotation of the handle 730—to facilitate generation of torque to overcome force resulting from internal pressure and advance the plunger 720 at high internal pressures.

Furthermore, rotation of the handle 730 using the crank member 732 can also provide for an increase in rotational speed of the handle 730. Rotation of the handle 730 using the crank member 732 can also provide for manual rotation of the handle 730 over 1, 2, 3 or more revolutions without requiring the practitioner to ungrasp and regrasp the grip 734, crank member 732, handle 730 or any portion of the inflation device assembly 700. In other words, when grasping the grip 734, a practitioner may rotate the handle 730 over multiple revolutions without releasing the grip 734, without pausing to reorient the wrist or handgrip as may be needed when rotating the handle 730 by just grasping the handle 730.

The crank member 732 and the grip 734 can be disposed in an undeployed state as shown in FIG. 7A for use in direct longitudinal displacement of the handle 730 or direct rotation of the handle 730. The crank member 732 and the grip 734 can also be disposed in a deployed state to facilitate rotatable operation of the inflation device assembly 700 when use of the crank member 732 is desired. In the undeployed state, the crank member 732 may be substantially disposed along the length of the handle 730 and may comprise a top portion 736 of the handle 730 that is hingedly coupled to a bottom portion 738 of the handle 730. In some embodiments the grip 734 may be nested, partially enclosed within or otherwise disposed parallel with or laterally adjacent to the crank member 732 in the undeployed state. The grip 734 may also be disposed on the top or exterior of the crank member 732 in the undeployed state.

FIG. 7B shows the crank member 732 in the deployed state. The crank member 732 is shown rotated approximately 180 degrees about a hinge point 740 to a position substantially parallel to the longitudinal axis of the handle 730 and substantially perpendicular to the longitudinal axis of the plunger 720. The grip 734 is also shown rotated approximately 90 degrees about a hinge point 742 to a position substantially parallel to the longitudinal axis of the plunger 720 and substantially perpendicular to the longitudinal axis of the handle 730. Other angular positions of the crank member 732 and the grip 734 relative to the plunger 720 and handle 730 are also contemplated and within the scope of this disclosure. For example, in some procedures or therapies, it may be more ergonomic for the longitudinal axis of the handle 730 to be at an angle other 90 degrees to the longitudinal axis of the plunger 720 such as between 70 and 90 degrees. Regardless of the deployment angles of the crank member 732 or the grip 734, the grip 734 may be rotatably coupled to the crank member 732 so that the grip 734 can rotate about its longitudinal axis in any such deployed state. Additionally, the handle 730 may also comprise a mechanism for releasably securing the crank member 732 and the grip 734 in their respective deployed positions, i.e. detents, friction, etc.

The state of the crank member 732 may change from the undeployed state to the deployed state and back several times during use of the inflation device assembly 700. Deployment of the crank member 732 may comprise hingedly rotating the crank member 732 about the hinge point 740 approximately 180 degrees from the undeployed position to a position extending from and substantially parallel to the longitudinal axis of the handle 730. Deployment of the crank member 732 may comprise hingedly rotating the grip 734 approximately 90 degrees about the hinge point 742 from a position laterally adjacent to the crank member 732 to a position substantially parallel to the longitudinal axis of the plunger 720. (As noted above, other deployment angles are within the scope of this disclosure.) Restoring the crank member 732 to the undeployed state may, in turn, comprise rotating the grip 734 to a position parallel with the crank member 732 and rotating the crank member 732 to a position parallel to the handle 730. The rotation of the crank member 732 and/or the grip 734 may be manually performed by the practitioner.

In some embodiments, the handle 730 may comprise a releasable securing feature 744 to prevent inadvertent deployment of the crank member 732 from the undeployed state. The securing feature 744 may comprise a snap fit or any suitable mechanism to prevent undesired rotation of the crank member 732 such as a latch, detent, friction, etc. One example of the securing feature 744 is shown at the end of the crank member 732 opposite the hinge point 740 comprising a pair of complimentary engagement components on the crank member 732 and bottom portion 736 of the handle 730. The securing feature 744 may be located at any position along the length of the handle 730 or the crank member 732. The securing feature 744 may comprise audible or tactile feedback indicating complete engagement of the securing feature 744. The securing feature 744 may be engaged by rotating the crank member 732 to the fully undeployed position. The securing feature 744 may be released or overcome by direct rotation of the crank member 732 about hinge point 740 by the practitioner.

The handle 730 may comprise a release mechanism for disabling the securing feature 744 and allowing the crank member 732 to rotate away from the undeployed state. FIGS. 7A and 7B show the handle 730 comprising a depressible member 743 configured to release or overcome the securing feature 744 upon depression by the practitioner. An example of a depressible member 743 is shown in FIG. 7B as a tab flexibly coupled to the crank member 732 such that inward depression of the tab releases the securing feature 744 and allows the crank member 732 to rotate about the hinge point 740 from the undeployed state to the deployed state. The depressible member 743 may be a button, lever, tab or any suitable component actuatable by the practitioner. The depressible member 743 may also be located at any position along the length of, or on any side of, the handle 730 or the crank member 732. The depressible member 743 may be a separate component or a flexible portion of either the handle 730 or the crank member 732. The depressible member 743 may also comprise a separate biasing member, i.e. a torsional, leaf or coil spring. The depressible member 743 may be hingedly or slidably coupled to the handle 730 or crank member 732.

The handle 730 may also comprise various forms of automation to facilitate deployment of the crank member 732. The rotation of the crank member 732 about the hinge point 740 and the rotation of the grip 734 about the hinge point 742 may be independent or linked such that rotation of the grip 734 is a direct result of rotation of the crank member 732. The handle 730 may comprise a biasing member to urge the crank member 732 away from the undeployed state to the deployed state. For example, the biasing member may be a torsional spring operably coupled to the handle 730 and crank member 732 adjacent hinge point 740 such that the crank member 732 is continuously biased to the fully deployed position. In other embodiments, the biasing member may urge the crank member 732 to only a partially deployed position. Other forms of biasing are within the scope of this disclosure such as leaf and coil springs as well as flexible portions of the handle 730 and/or crank member 732. Still further, a linkage—such as a four bar mechanism—or other mechanism may be configured to automatically deploy the grip 734 from the crank member 732 as the crank member 732 rotates about the hinge point 740. Other mechanisms, including compliant mechanisms are within the scope of this disclosure.

Still further, the crank member 732 may comprise a biasing member (in addition to a biasing member in connection with the crank member 732 or independent thereof) to urge the grip 734 from the undeployed state to the deployed state. In some embodiments, the biasing member may be a torsional spring operably coupled to the crank member 732 and grip 734 adjacent hinge point 742 such that the grip 734 is continuously biased to the fully deployed position. In other embodiments, the biasing member may urge the grip 734 to only a partially deployed position. Other forms of biasing are within the scope of this disclosure such as leaf and coil springs as well as flexible portions of the handle 730, crank member 732 and/or grip 734. Further, linkages, mechanisms (including compliant mechanisms) may also be configured to facilitate deployment of the grip 734.

In some embodiments, returning the crank member 732 to the deployed state may comprise overcoming a biasing member associated with the grip 734 and a biasing member associated with the crank member 732 while rotating the grip 734 and crank member 732 to their respective undeployed positions, and, in some instances, reengaging the securing feature 744.

Rotation of the handle 730 through use of the crank member 732 may facilitate speed of rotation as well as increased leverage. The relative benefits of speed and leverage can shift depending on the fluid pressure in the syringe body 712 and required plunger 720 displacement. In some cases high leverage with low speed is ergonomically optimal and in other cases high speed with low leverage is optimal. Ergonomically speaking, the torque benefit associated with a longer lever may be inversely proportion to the speed benefit. Said another way, it may be more ergonomic to rotate a shorter lever than a longer lever at a higher speed. Hence, when cranking against lower pressures, it may be advantageous to position the grip 734 at a shorter radial offset position from the longitudinal axis of the plunger 720. Since during use, pressure and plunger 720 displacement vary, in some procedures it may be advantageous to have the grip 734 positionable to various radial offset locations relative to the longitudinal axis of the plunger 720 in the deployed state. FIG. 7B shows the grip 734 located substantially at the extended end of the crank member 732. Also shown in phantom lines are two additional potential positions of the grip 734 along the length of the crank member 732. As also explained below, the grip 734 may be positionable at discrete positions along the length of the crank member 732, or may be positionable at any point along a continuous portion of the crank member 732.

FIG. 7B shows an example of slidable engagement of the grip 734 to the crank member 732 to facilitate varying the position of the grip 734 along the length of the crank member 732. In the depicted example, the crank member 732 is shown comprising a pair of complimentary track slots 747 through both lateral walls of the crank member 732. The hinge point 742 comprises a hinge pin 749 which extends laterally through the track slots 747 of each side wall. The track slots 747 extend along at least a portion of length of the crank member 732 and allow the hinge pin 749 and consequently the hinged end of the grip 734 to slidably move within the track slots 747. Other suitable slidable engagement methods to facilitate positioning of the grip 734 with respect to the crank member 732 as could be contemplated by a person of ordinary skill in the art are within the scope of this disclosure. As noted above, the grip 734 may freely side along the track slots 747 or the crank member 732 may comprise a mechanism to at least partially constrain the sliding motion.

The crank member 732 may also comprise a feature for securing the grip 734 in discrete radially offset positions from the longitudinal axis of the plunger 720. FIG. 7B shows an exemplary feature for defining discrete positions of grip 734 along the length of the track slots 747. The track slots 747 are shown comprising notches 748 on the upper surface of both track slots 747. The notches 748 are configured in complimentary pairs to accommodate end portions of the hinge pin 749 at discrete locations along the length of the track slots 747. In this example the grip 734 is biased toward the notched side of the track slots 747 such that when properly positioned, the end portions of the hinge pin 749 are urged into and engage one of the complimentary pairs of notches 748. Any suitable mechanisms for biasing the grip 734 toward the notched side of the track slots 747 such as a leaf spring disposed along an inner surface of the crank member 732, a coil spring disposed on the end of the grip 734, a flexible portion of the crank member 732 and/or grip 734, etc. are within the scope of this disclosure. The example depicted in FIG. 7B, shows five discrete pairs of notches 748 along the length of the track slots 747. However, any number of discrete positions are within the scope of this disclosure. The number of discrete positions could be 2, 3, 4, 5, or more. In other embodiments, the track slots 747 may also comprise a rough upper surface providing at least some resistance to sliding of the hinge pin 749 over a substantially continuous range of the length of the track slots 747. Any suitable mechanisms for defining discrete positions of the grip 734 along the length of the crank member 732 are within the scope of this disclosure.

Though the description above relates to certain potential embodiments of how the grip 734 may be displaceable along the length, or a portion of the length, of the crank member 732, various other methods and structures for varying the position of the grip 734 are within the scope of this disclosure. As noted above the grip 734 may be positionable at discrete points or at any points along a continuous length of the crank member 732. Furthermore, in embodiments wherein the grip 734 is positionable at any point along a continuous length of the crank member 732, displacement of the grip 732 may be constrained such that it tends to stay in a particular position once initially positioned therein, and thus tends to stay in a selected position during use, or it may be free to move along the continuous length during use.

Use of the inflation device assembly 700 may comprise several operations. The practitioner may initially advance the plunger 720 directly by disengaging the thread rail 724 from the coupling member 718 and applying direct longitudinal force on the handle 730, for example until the force required to overcome the pressure becomes ergonomically difficult. At such a point, the practitioner may then advance the plunger 720 by rotating the handle 730 about its axis. The practitioner may then deploy the crank member 732 and/or grip 734 to facilitate this rotation. Deployment may comprise actuating the depressible member 743 to release securing feature 744. In some such embodiments, once released, the crank member 732 may automatically rotate about hinge point 740 away from the undeployed state to the deployed state due to a biasing force. The grip 734 may also automatically rotate about the hinge point 742 away from the undeployed state to the deployed state due to a biasing force. As stated above, such biasing of the crank member 732 and the grip 734 may only urge the crank member 732 and grip 734 to partially deployed states whereupon the practitioner may manually complete the deployment of each.

The practitioner may then grasp the grip 734 and advance the plunger 720 by rotating the crank member 732 one or several revolutions without ungrasping the grip 734.

During or before rotation of the handle 730, the practitioner may also reposition the grip 734 from the initial deployment position which may be the maximum radial distance from the longitudinal axis of the plunger 720 to a position radially closer to the longitudinal axis of the plunger 720 due to a relatively low pressure in the syringe body 712. The practitioner may then rotatably advance the plunger 720 until it becomes advantageous to reposition the grip 734 further from the longitudinal axis of the plunger 720 due to a relatively high pressure in the syringe body 712. Repositioning of the grip 734 may include disengaging a feature configured to constrain the grip 734 at discrete positions (or at a preselected position along a continuous length) prior to sliding the grip 734 to a different position and then reengaging the feature. Thereafter the practitioner may continue rotatably advancing the plunger 720. The practitioner may also return the crank member 732 to the undeployed state by hingedly rotating the grip 734 and the crank member 732 back to their respective undeployed positions and engaging the securing feature 744. The practitioner may retract the plunger 720 by rotating the plunger 720 or by disengaging the thread rail 724 from the coupling member 718 and directly retracting the plunger 720. While specific orders of the described operations may be advantageous, no specific order is required and each operation is optional.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. An inflation device assembly, comprising:
 a syringe body;
 a plunger configured for advancement and retraction within the syringe body; and
 a coupling member comprising coupling member threads configured to constrain movement of the plunger within the syringe body;
 a handle coupled to a proximal portion of the plunger; and
 an extendable and non-detachable crank member coupled to the handle;
 wherein the plunger comprises plunger threads configured to be selectively engaged and disengaged with the coupling member threads, wherein the plunger threads are configured to be retractable from the coupling member threads,
wherein the crank member is configured to be disposed in a deployed state and an undeployed state,
wherein the crank member comprises a grip to facilitate a practitioner's grasp of the crank member with the practitioner's hand or fingers, and
wherein the grip is oriented substantially parallel to a longitudinal axis of the plunger when in the deployed state and oriented substantially orthogonal to the longitudinal axis of the plunger when in the undeployed state.

2. The inflation device assembly of claim 1, wherein a portion of the crank member extends from the handle in a direction radially from the longitudinal axis of the plunger.

3. The inflation device assembly of claim 2, wherein the portion of the crank member extending from the handle extends in a direction substantially perpendicular to the longitudinal axis of the plunger.

4. The inflation device assembly of claim 1, wherein the grip is rotatably coupled to the crank member.

5. The inflation device assembly of claim 1, wherein in the deployed state, the crank member extends radially from the handle and in the undeployed state, the crank member is substantially disposed along a length of the handle.

6. The inflation device assembly of claim 1, wherein the grip is oriented substantially parallel to a longitudinal axis of the handle when in the undeployed state.

7. The inflation device assembly of claim 1, wherein the grip is positionable at least two discrete offset radial positions from the longitudinal axis of the plunger.

8. The inflation device assembly of claim 1, wherein the crank member is hingedly coupled to the handle and the grip is hingedly coupled to the crank member.

9. The inflation device assembly of claim 8, wherein the grip is biased away from the undeployed state.

10. The inflation device assembly of claim 8, wherein the crank member is releasably secured to the handle in the undeployed state.

11. The inflation device assembly of claim 10, wherein the handle comprises a release mechanism configured to release the crank member from the undeployed state.

12. The inflation device assembly of claim 1, wherein the grip is slidably positionable along a portion of a length of the crank member.

13. The inflation device assembly of claim 12, wherein the grip is positionable at any point along a continuous portion of the crank member.

14. The inflation device assembly of claim 12, wherein the grip is positionable at two or more discrete positions along the portion of the length of the crank member.

15. The inflation device assembly of claim 1, wherein the grip is disposed within the handle in the undeployed state.

16. A method of pressurizing a medical device, comprising:
obtaining an inflation device comprising a syringe body, a plunger disposed at least partially within the syringe body, a handle coupled to the plunger, and an extendable and non-detachable crank member coupled to the handle;
extending the crank member radially from a longitudinal axis of the plunger;
deploying a grip from a position laterally adjacent to the crank member;
positioning the grip from a first position that is orthogonal to the longitudinal axis of the plunger to a second position along at least a portion of a length of the crank member, wherein the grip is parallel to the longitudinal axis of the plunger in the second position; and
advancing the plunger by grasping the syringe body in one hand and rotating the crank member with a second hand.

17. The method of claim 16, further comprising:
disengaging a thread rail of the plunger from the syringe body;
advancing the plunger through longitudinal movement of the handle to a first internal pressure;
re-engaging the thread rail of the plunger to the syringe body after reaching the first internal pressure;
advancing the plunger by rotating the crank member clockwise to a second internal pressure;
disengaging the thread rail of the plunger from the syringe body after reaching the second internal pressure; and
retracting the plunger through longitudinal movement of the handle.

18. The method of claim 16, further comprising:
rotating the crank member at least one full revolution without ungrasping the inflation device.

19. The method of claim 16, wherein the grip is disposed within the handle in the first position.

20. An inflation device assembly, comprising:
a syringe body;
a plunger configured for advancement and retraction within the syringe body;
a handle coupled to a proximal portion of the plunger;
a coupling member comprising threads configured to longitudinally displace the plunger within the syringe body upon rotation of the plunger about a longitudinal axis of the plunger;
an extendable and non-detachable crank member coupled to the handle;
wherein the crank member is configured to be disposed in a deployed state and an undeployed state,
wherein the crank member is oriented substantially orthogonal to a longitudinal axis of the plunger when in the deployed state and when in the undeployed state, and
wherein the crank member is configured to be rotated by a practitioner at least one full revolution without ungrasping and regrasping the inflation device.

21. The inflation device assembly of claim 20, wherein the crank member comprises a grip to facilitate a practitioner's grasp of the crank member with the practitioner's hand or fingers, and wherein the grip is disposed within the handle in the undeployed state.

* * * * *